US012156950B2

(12) United States Patent
Jorgenson et al.

(10) Patent No.: US 12,156,950 B2
(45) Date of Patent: Dec. 3, 2024

(54) SOFTWARE ARCHITECTURE AND SYSTEM FOR DELIVERING SELECTED SANITATION PROTOCOLS FOR MULTIPLE PATHOGENS AND PESTS

(71) Applicant: BWR Innovations LLC, Fargo, ND (US)

(72) Inventors: Joel A. Jorgenson, Fargo, ND (US); Thomas W. Nelson, Burnsville, MN (US); Adam C. Jorgenson, West Fargo, ND (US)

(73) Assignee: BWR Innovations LLC, Fargo, ND (US)

( * ) Notice: Subject to any disclaimer, the term of this patent is extended or adjusted under 35 U.S.C. 154(b) by 969 days.

(21) Appl. No.: 16/923,711

(22) Filed: Jul. 8, 2020

(65) Prior Publication Data

US 2022/0011746 A1 Jan. 13, 2022

(51) Int. Cl.
*A61L 2/04* (2006.01)
*A01M 1/20* (2006.01)
(Continued)

(52) U.S. Cl.
CPC ............. *A61L 2/04* (2013.01); *A01M 1/2094* (2013.01); *A61L 2/06* (2013.01); *A61L 2/10* (2013.01);
(Continued)

(58) Field of Classification Search
CPC ............................... A61L 2/04; A01M 1/2094
See application file for complete search history.

(56) References Cited

U.S. PATENT DOCUMENTS

| 3,784,896 A | 1/1974 | Lakota |
| 4,905,134 A | 2/1990 | Recker |

(Continued)

FOREIGN PATENT DOCUMENTS

| WO | 02066974 A2 | 8/2002 |
| WO | 2020/047075 A1 | 3/2020 |

OTHER PUBLICATIONS

PCT International Search Report and Written Opinion for PCT/US20/41317; Oct. 1, 2020.

(Continued)

*Primary Examiner* — Kevin Joyner
(74) *Attorney, Agent, or Firm* — Neustel Law Offices

(57) ABSTRACT

A software architecture and system for delivering selected sanitation protocols for multiple pathogens and pests for sanitizing a physical space. The software architecture and system generally includes a plurality of protocol identifiers linked to sanitation protocols arranged as pages in a protocol storage. Each sanitation protocol comprises a plurality of parameters arranged in tabular form for carrying out a sanitation process for one or more pathogens and/or pests. Also included are a control panel/display, controller, heat source, UV light source, and sensors. The protocol identifiers are displayed on the control panel/display and the controller retrieves the parameters of a selected sanitation protocol from the protocol storage. The controller operates in a closed-loop control arrangement with the heat source, UV light source, and sensors to automatically carry out a sanitation process according to the parameters of the selected sanitation protocol.

21 Claims, 9 Drawing Sheets

(51) Int. Cl.
  *A61L 2/06* (2006.01)
  *A61L 2/10* (2006.01)
  *A61L 2/24* (2006.01)
(52) U.S. Cl.
  CPC ............. *A61L 2/24* (2013.01); *A61L 2202/11* (2013.01); *A61L 2202/14* (2013.01)

(56) References Cited

U.S. PATENT DOCUMENTS

| | | | |
|---|---|---|---|
| 4,937,462 | A | 6/1990 | Recker |
| 5,317,500 | A | 5/1994 | Iden |
| 5,642,006 | A | 6/1997 | Cech |
| 5,767,591 | A | 6/1998 | Pinkerton |
| 6,080,500 | A | 6/2000 | Fuju |
| 6,112,136 | A | 8/2000 | Paul |
| 6,169,390 | B1 | 1/2001 | Jungreis |
| 6,172,432 | B1 | 1/2001 | Schnackenberg |
| 6,184,593 | B1 | 2/2001 | Jungreis |
| 6,239,997 | B1 | 5/2001 | Deng |
| 6,503,649 | B1 | 1/2003 | Czajkowski |
| 6,657,319 | B2 | 12/2003 | Sanada |
| 7,180,210 | B1 | 2/2007 | Jorgenson |
| 7,222,001 | B2 | 5/2007 | Frost |
| 8,203,231 | B2 | 6/2012 | Knepple |
| 2002/0114983 | A1 | 8/2002 | Frank |
| 2005/0183895 | A1 | 8/2005 | Severns |
| 2007/0193999 | A1 | 8/2007 | Peterson |
| 2007/0258865 | A1* | 11/2007 | Yamasaki ............... A61L 9/145 422/124 |
| 2007/0264537 | A1 | 11/2007 | Huang |
| 2009/0025315 | A1 | 1/2009 | Gutfleisch |
| 2009/0055031 | A1 | 2/2009 | Slota |
| 2012/0139354 | A1 | 6/2012 | Said |
| 2012/0282135 | A1 | 11/2012 | Trapani |
| 2013/0183749 | A1 | 7/2013 | Aamodt |
| 2015/0013063 | A1* | 1/2015 | Boodaghians ......... B64D 11/02 4/663 |
| 2015/0217869 | A1 | 8/2015 | Brunaux |
| 2015/0378745 | A1 | 12/2015 | He |
| 2017/0116669 | A1 | 4/2017 | Wickstrom |
| 2018/0343847 | A1* | 12/2018 | Ervin .................... A01M 1/226 |
| 2019/0321500 | A1 | 10/2019 | Anderson |
| 2020/0075972 | A1 | 3/2020 | Jorgenson |

OTHER PUBLICATIONS https://www.prolampsales.com/blogs/specialty-architectural-lighting/how-to-calculate-uv-c-dose-on-a-surface; ProLampSales Website Blog Post; Apr. 16, 2020.
Synchrotact 5 Synchronizing and Paralleling Equipment and Systems for Synchronous Machines and Networks by ABB Automation; Exact Publication Date Unknown (Prior to Apr. 2004).
A Fast Following Synchonizer of Generators; IEEE Transaction of Energy Conversaion, vol. 3, No. 4; Dec. 1988.
High Integrity Power Control Systems for Critical Facilities by Russelectric; Exact Publication Date Unknown (Prior to Apr. 2004).
PCT International Search Report and Written Opinion for PCT/US2020/015545; Received on Apr. 28, 2020.
http://www.altergy.com/wp-content/uploads/2017/09/Altergy_Cable_Data_sheet_ATP_web.pdf; Altergy Cable/Multiple-System Operators Data Sheet; Received Aug. 28, 2019.
http://www.altergy.com/wp-content/uploads/2016/08/Altergy_CorpBro_Web_singlePg.pdf; Altergy Corporate Brochure; Received Aug. 28, 2019.
http://www.altergy.com/wp-content/uploads/2017/09/Altergy_Nacelle_Data_sheet_ATP_web.pdf; Altergy Freedom Power System Nacelle Data Sheet; Published Feb. 2017.
http://www.altergy.com/wp-content/uploads/2017/09/Altergy_PSP_Data_sheet_6_ATP_web.pdf; Altergy Public Safety Platform Data Sheet; Published 2017.
http://www.altergy.com/wp-content/uploads/2017/09/Altergy_Reformer_Data_sheet_7_ATP_web.pdf; Altergy Freedom Power System (FPS-EX) Data Sheet; Published Jun. 2018.
http://www.altergy.com/wp-content/uploads/2018/07/Altergy_TSP_Data_sheet_2018_ATP_web.pdf; Altergy Traffic Signal Platform (TSP) Data Sheet; Published 2018.
http://www.altergy.com/products-2/enclosures/; Altergy Enclosures Webpage; Received Aug. 28, 2019.
http://www.altergy.com/products-2/mobile-solutions/; Altergy Mobile Solutions Webpage; Received Aug. 28, 2019.
https://www.hydrogenics.com/hydrogen-products-solutions/fuel-cell-power-systems/; Hydrogenics HyPM-HD Power Modules Brochure; Published Feb. 2018.
https://www.hydrogenics.com/technology-resources/media-downloads-table/; Hydrogenics HyPM-XR Back-Up Power Fuel Cell Brochure; Published May 2016.
https://www.hydrogenics.com/technology-resources/media-downloads-table/; Hydrogenics HyPM Rack Brochure; Published Mar. 2014.
https://www.intelligent-energy.com/uploads/product_docs/49087_IE_-_FCM_brochure_May_2018.pdf; Intelligent Energy 800 Series Fuel Cell Module Brochure; Published May 2018.
https://www.intelligent-energy.com/uploads/product_docs/Final_UAV_brochure_Sept_2018_web.pdf Intelligent Energy UAV Fuel Cell Power Module Brochure; Published Aug. 2018.
https://www.plugpower.com/wp-content/uploads/2016/03/2016_GenKey_Stationary020816.pdf; Plug Power GenKey for Stationary Power Brochure; Published Feb. 8, 2016.
https://www.plugpower.com/wp-content/uploads/2018/06/2018GenKeyBrochure_F1Digi-1.pdf; Plug Power GenKey for Material Handling Brochure; Published Jun. 2018.
https://www.plugpower.com/products/progen/fuel-cells-for-industrial-robotics/; Plug Power ProGen Fuel Cells for Industrial Robotics Webpage; Received Aug. 28, 2019.
https://www.arema.org/files/library/2014_Conference_Proceedings/Fuel_Cell_Technology_For_Backup_And_Supplemental_Power_Applications.pdf; Arema Fuel Cell Article; Jun. 13, 2014.
https://www.plugpower.com/wp-content/uploads/2015/05/Intelec2011_ReliOn_P081_IEEE.pdf; ReliOn Smart Energy Solutions Article; Joe Blanchard; Published Nov. 2011.
https://www.plugpower.com/wp-content/uploads/2015/05/ReliOnIntelec_2013Paper.pdf; ReliOn Superstorm Sandy: Fuel Cell Design Article; Spink and Saathoff; Published 2013.
https://www.plugpower.com/wp-content/uploads/2018/06/2018_GenFuelSpec_F1Digi.pdf; Plug Power GenFuel Hydrogen Solutions for Material Handling Applications; Published Jun. 2018.
https://www.plugpower.com/wp-content/uploads/2016/03/GenSureProductCatalogsm_012716.pdf; Plug Power GenSure Fuel Cell Systems Product Catalog; Published Mar. 2016.
https://www.plugpower.com/wp-content/uploads/2014/12/ColdStorageDigi_F_101716.pdf; Plug Power GenDrive Fuel Cells for Cold Chain Environments Brochure; Published Dec. 2014.
https://www.plugpower.com/wp-content/uploads/2016/07/Mfg_mktg_Final072216.pdf; Plug Power Fuel Cells for Manufacturing Facilities Brochure; Published Jul. 2016.
https://www.plugpower.com/wp-content/uploads/2019/04/ProGenSpec_Mobility_Digi0219.pdf; Plug Power ProGen Fuel Cell Power for E-Mobility Applications; Published Apr. 2019.
PCT International Search Report and Written Opinion for PCT/US2019/48543; Nov. 27, 2019.
https://www.energy.gov/sites/prod/files/2015/11/f27/fcto_fuel_cells_fact_sheet.pdf; Fuel Cell Technologies Office Fact Sheet; Nov. 2015.
https://www.energy.gov/eere/fuelcells/fuel-cell-systems; Office of Energy Efficiency & Renewable Energy Fuel Cell Systems Article; Jan. 26, 2017.
https://www.cdc.gov/infectioncontrol/pdf/guidelines/disinfection-guidelines-H.pdf; Guideline for Disinfection and Sterilization in Healthcare Facilities Article; Rutala; 2008.
https://www.ncbi.nlm.nih.gov/pmc/articles/PMC7201869/pdf/TRF-46-1770.pdf; Evaluation of Inactivation Methods for Severe Acute Respiratory Syndrome Coronavirus in Noncellular Blood Products by Miriam E.R. Darnell and Deborah R. Taylor; The Journal of Aabb Transfusion; Oct. 2006.

(56) References Cited

OTHER PUBLICATIONS https://www.ncbi.nlm.nih.gov/pmc/articles/PMC4181824/pdf/irv0008-0585.pdf; Heat Inactivation of the Middle East Respiratory Syndrome Coronavirus by India Leclercq; U.S. National Library of Medicine Influenza Journal; Jun. 24, 2014.
https://www.tandfonline.com/doi/pdf/10.1080/01478885.2020.1734718?needAccess=true; Coronavirus Disinfection in Histopathology by Anthony F. Henwood, Journal of Histotechnology; Mar. 1, 2020.
https://www.ncbi.nlm.nih.gov/pmc/articles/PMC7179540/pdf/drm-0212-0119.pdf; Inactivation of SARS Coronavirus by Means of Povidone-Iodine, Physical Conditions and Chemical Reagents by Hiroaki Kariwa; Dermatology; Feb. 2006.
https://www.ncbi.nlm.nih.gov/pmc/articles/PMC7086689/pdf/430_2004_Article_219.pdf; Stability and Inactivation of SARS Coronavirus by H. F. Rabenau; Med Microbiol Immunol; Apr. 29, 2004.
https://www.ncbi.nlm.nih.gov/pmc/articles/PMC7112912/pdf/main.pdf; Inactivation of the Coronavirus that Induces Severe Acute Respiratory Syndrome, SARS-COV by Miriam E.R. Darnell; Journal of Virological Methods; Aug. 3, 2004.
https://www.ncbi.nlm.nih.gov/pmc/articles/PMC7169306/pdf/VOX-87-302.pdf; Heat Sensitivity of a SARS-Associated Coronavirus Introduced Into Plasma Products by M. Yunoki; Vox Sanguinis; Sep. 10, 2004.
https://pubmed.ncbi.nlm.nih.gov/15323569/; Low Stability of Nucleocapsid Protein in SARS Virus by Yulong Wang; Abstract of Article from Biochemistry; Aug. 31, 2004.
https://pubmed.ncbi.nlm.nih.gov/14631830/; Stability of SARS Coronavirus in Human Specimens and Environment and Its Sensitivity to Heating and UV Irradiation by Shu-Ming Duan; Abstract of Article from Biomed Environ Sci.; Sep. 2003.

\* cited by examiner

SOFTWARE ARCHITECTURE AND SYSTEM FOR DELIVERING SELECTED SANITATION PROTOCOLS FOR MULTIPLE PATHOGENS AND PESTS

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

Field

Example embodiments in general relate to a software architecture and system for delivering selected sanitation protocols for multiple pathogens and pests for sanitizing a physical space or area.

Related Art

Any discussion of the related art throughout the specification should in no way be considered as an admission that such related art is widely known or forms part of common general knowledge in the field.

There exist a number of methods to sanitize physical spaces or areas in order to treat infestations of unwanted pests, such as bed bugs, cockroaches, mosquitoes, or mites. Chemical treatment is a common approach, where chemicals are spread in solid, liquid, or gaseous forms to treat a room and/or equipment. However, there are multiple issues with chemical treatments. The chemicals applied may leave behind undesirable residues that are messy and require clean-up. The chemicals and chemical residues may result in incidental damage to assets, for example the chemicals may be absorbed in furniture and may require the furniture to be thoroughly cleaned or even discarded. The target pests may have or may develop resistance to the applied chemicals. Chemical treatments may also incur high recurring costs, including material costs.

In addition to pests, pathogens such as coronavirus (CoV), *Clostridium difficile* (C diff), influenza, and other pathogens and microorganisms, both known and as yet unknown, present considerable health threats to people in their homes, and in hospitals, hotels, nursing and assisted care facilities and other facilities. Chemical applications are used to sanitize physical spaces to treat such pathogens and microorganisms. However, the use of chemicals to treat target pathogens raises the same concerns as it does for treating target pests.

In addition, especially in environments like those described above, the use of chemical treatments raises additional concerns. While it is unlikely a physical space of a hotel or nursing care facility will be infested with a whole host of different pests, it is a very likely scenario that a physical space of a public hotel, hospital, or other healthcare or residential facility may be exposed to and may contain multiple different types of potentially harmful pathogens and other microorganisms, including one or more of those described above. Since each different pathogen may require a different chemical formulation to treat, in order to sanitize a physical space and treat a broad spectrum of pathogens may require multiple applications of different chemicals. This compounds the issues and problems related to the use of chemical treatments and may create additional issues and problems, for example the possibility of unintended and undesirable cross-reactions between the chemicals used.

A non-chemical approach exists that avoids the various limitations of chemical treatments. A suitable application of heat or ultraviolet (UV) light can be effective to treat against specific target pests and pathogens. For example, a suitable application of heat can desiccate adults, larvae, or eggs of a wide variety of pests without the chemical residues, resistances, and other issues that accompany the use of chemical treatments. Also for example, a suitable application of UV light can be effective to disrupt the RNA of a wide variety of pathogens which can cause the pathogens to become inactive and unable to replicate.

An issue with the use of heat and/or UV light as a treatment for pests and pathogens is the amount of electricity required to power electric heat and UV light sources. For example, at least 15 kW to 20 kW of electrical power is generally required to operate a suitable electric heat source to heat a typical hotel, hospital, or care facility room to an effective target temperature. The electrical wiring standards typically employed in such buildings per the National Electrical Code (NEC) share a single fifteen (15) ampere/120 volt circuit between three rooms, but the electricity needed to produce 15 kW of electrical power requires the equivalent of nine (9) conventional fifteen (15) ampere/120 volt circuits. Since the typical building electrical infrastructure is thus inadequate to meet the electrical need, a separate electrical source is required.

BWR Innovations, LLC, the assignee of the present application, has developed a fuel cell generator that is capable of operating safely indoors and of providing at least 20 kW of energy suitable for powering heat and UV light sources. The combination of heat and UV light produced can provide an effective, safe, and cost-effective means to treat a wide spectrum of pests and pathogens.

Another issue involved in treating a wide variety of different pests and pathogens is the numerous different treatment or sanitation protocols, large number of different parameters and combinations of parameters, and numerous different sanitation processes that are required. As a result, a substantial amount of operator or user manual involvement and intervention is required to set up, program, update, operate, and monitor treatment systems, equipment, and devices, to monitor physical conditions in the physical space or area being sanitized while sanitation processes are being carried out, and to make necessary in-process adjustments to the settings and operation of systems, equipment, and devices in accord with the protocols and parameters of a particular sanitation process. Besides the extensive amount of work this entails for operators and users, the substantial amount of manual intervention and involvement required can easily result in confusion and mistakes being made, which can result in the wrong sanitation processes being performed, or in sanitation processes not being carried out correctly and according to the proper protocols and parameters to effectively eradicate target pests and pathogens.

There is thus a need for a software architecture and system for delivering selected sanitation protocols for multiple pathogens and pests for sanitizing a physical space or area that can receive and retain in a logical and organized way a plurality of different sanitation protocols comprising a plurality of different operational parameters for carrying out a plurality of different sanitation processes. There is a need for such a software architecture and system that can present a plurality of different sanitation protocols comprising a plurality of different operational parameters for a plurality of target pests and pathogens so that they are readily identifiable and easily selectable by an operator. There is a need for such a software architecture and system that is able to carry out a plurality of different sanitation processes for a plurality of target pests and pathogens in a physical space or area according to a selected sanitation protocol comprising a plurality of operational parameters intelligently, automatically, and with minimal operator intervention and involvement. There is a need for such a software architecture and system in which the operational parameters are able to control substantially all functions of power generation, heat production, airflow and air distribution, UV light production, and telemetry data monitoring and gathering for a plurality of different sanitation processes. There is a need for such a software architecture and system in which each of a plurality of different sanitation protocols comprising a plurality of operational parameters for a plurality of target pests and pathogens can be easily and readily identified and accessed to add new protocols and parameters and to update existing protocols and parameters as new target pests, pathogens, and treatments are identified. There is also a need for such a software architecture and system for receiving, retaining and delivering a plurality of different sanitation protocols with a plurality of operational parameters that is operable in conjunction with a fuel cell system that generates operating power locally.

SUMMARY

An example embodiment is directed to a software architecture and system for delivering selected sanitation protocols for multiple pathogens and pests. The software architecture and system includes a plurality of selectable sanitation protocols. Each sanitation protocol is adapted to treat a corresponding target pathogen or pest or target group of pathogens or pests to sanitize a physical space.

A protocol storage is included for storing the plurality of sanitation protocols. According to one aspect of the software architecture and system, the plurality of sanitation protocols are arranged in the protocol storage as a plurality of successive pages, or as a plurality of pages linked in a chain. In one particular embodiment, the chain may be a two-way chain.

A plurality of protocol identifiers are also included. Each protocol identifier is selectable and comprises a link to a corresponding sanitation protocol in the protocol storage. According to one aspect of the software architecture and system, a display is included for displaying at least some of the plurality of protocol identifiers and a protocol selector is included for selecting a displayed protocol identifier.

A heat source for heating the physical space, and a UV light source for irradiating the physical space with UV radiation are included. A controller is included and is coupled to the protocol storage, the heat source, and the UV light source. The controller is configured to respond to a protocol identifier being selected to automatically control the operation of the heat source and the UV light source according to the corresponding sanitation protocol to sanitize the physical space against the corresponding target pathogen or pest or target group of pathogens or pests.

According to an aspect of the software architecture and system, each sanitation protocol comprises a plurality of protocol and operational parameters for controlling all aspects of the operation of the software architecture and system, including the operation of the heat source and the UV light source. The plurality of protocol parameters may comprise one or more of target temperature, temperature ramp rate, dwell time, UV light intensity, and exposure time.

According to yet another aspect, the software architecture and system includes at least one sensor in the physical space, and the controller, heat source UV light source, and sensor are coupled and operable in a closed-loop feedback control arrangement. The software architecture and system is thus adapted to automatically sanitize a physical space against a target pathogen or pest or target group of pathogens or pests according to the a selected sanitation protocol and with little or no manual operator intervention or involvement.

According to yet another aspect, the software architecture and system includes a remote upload unit for receiving and uploading sanitation protocols to the protocol storage. The upload unit comprises a user interface displaying a template comprising a plurality of fields for entering the protocol identifier and the plurality of parameters for each sanitation protocol.

According to yet another aspect, the software architecture and system includes a fuel cell system. The fuel cell system is adapted to locally generate hydrogen and to locally generate electrical operating power from the hydrogen to power the other components of the software architecture and system.

There has thus been outlined, rather broadly, some of the embodiments of a software architecture and system for delivering selected sanitation protocols for multiple pathogens and pests in order that the detailed description thereof may be better understood, and in order that the present contribution to the art may be better appreciated. There are additional embodiments of the software architecture and system that will be described hereinafter and that will form the subject matter of the claims appended hereto. In this respect, before explaining at least one embodiment of the software architecture and system in detail, it is to be understood that the software architecture and system are not limited in application to the details of construction or to the arrangements of the components set forth in the following description or illustrated in the drawings. The software architecture and system are capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 7 is a block diagram illustrating a closed-loop arrangement of components and protocols comprising a software architecture and system for delivering selected sanitation protocols for multiple pathogens and pests in accordance with an example embodiment.

FIG. 8 is a block diagram illustrating a protocol comprising a portion of a software architecture and system for delivering selected sanitation protocols for multiple pathogens and pests in accordance with an example embodiment.

DETAILED DESCRIPTION

Figure 1:
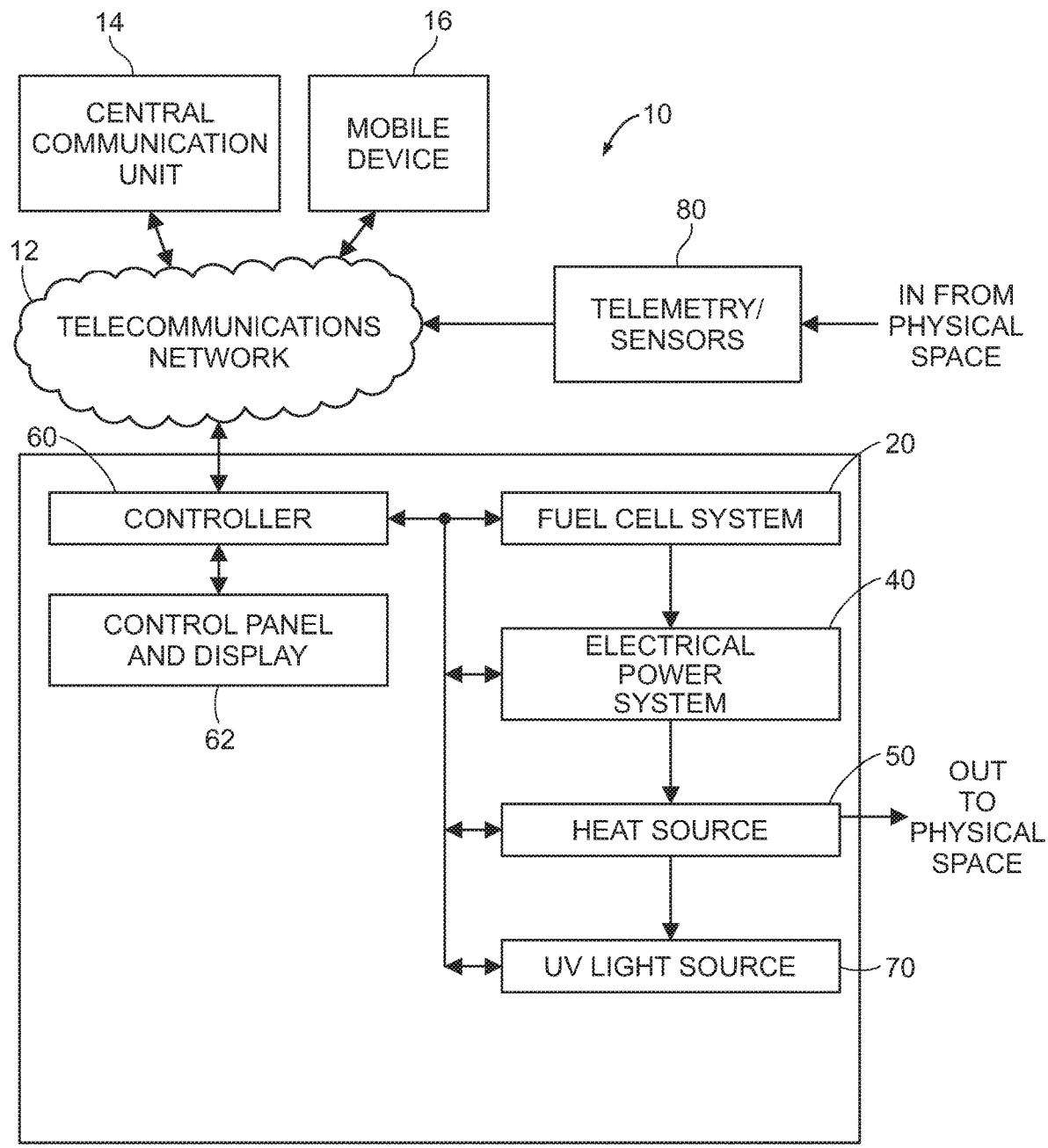
FIG. 1 is a block diagram illustrating the functional relationship between components of a software architecture and system for delivering selected sanitation protocols for multiple pathogens and pests in accordance with an example embodiment.
Figure 2:
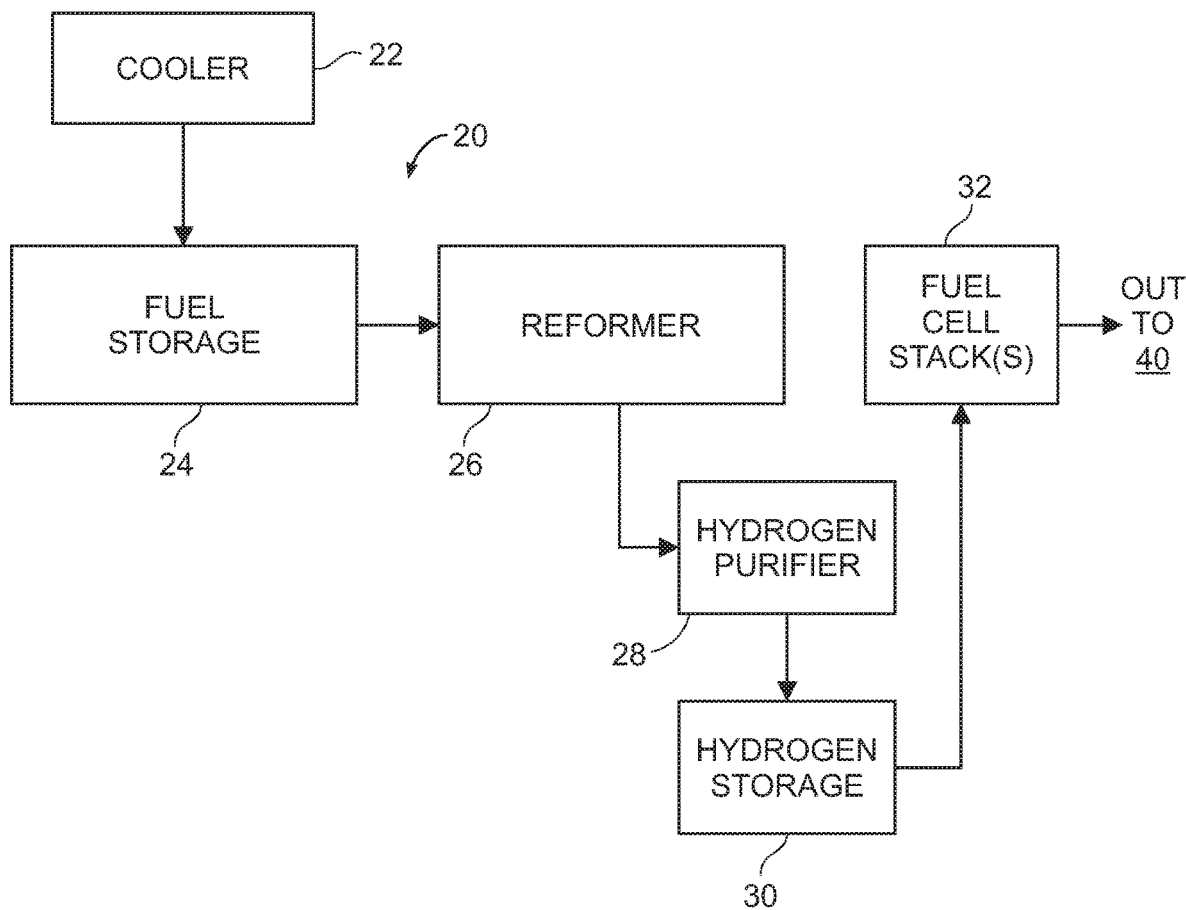
FIG. 2 is a block diagram illustrating components of a fuel cell system comprising a portion of a software architecture and system for delivering selected sanitation protocols for multiple pathogens and pests in accordance with an example embodiment.
Figure 3:
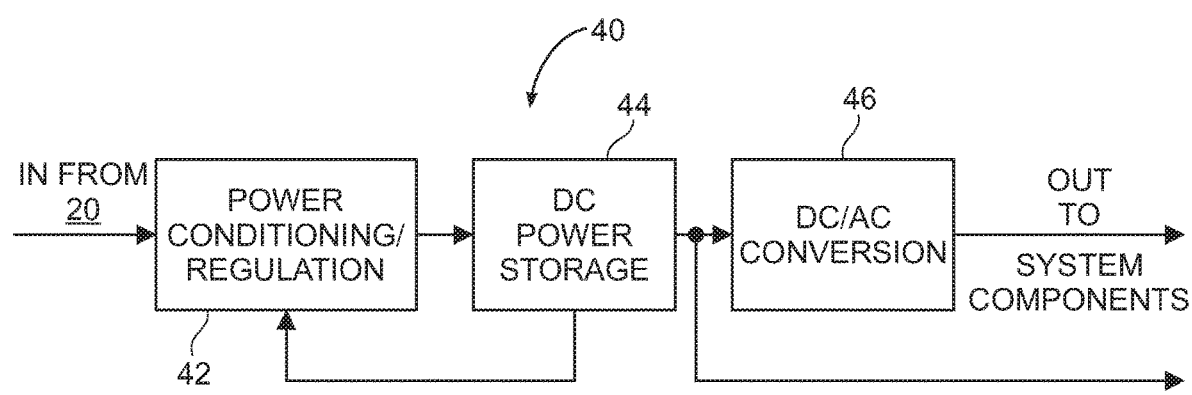
FIG. 3 is a block diagram illustrating components of an electrical power system comprising a portion of a software architecture and system for delivering selected sanitation protocols for multiple pathogens and pests in accordance with an example embodiment.
Figure 4A:
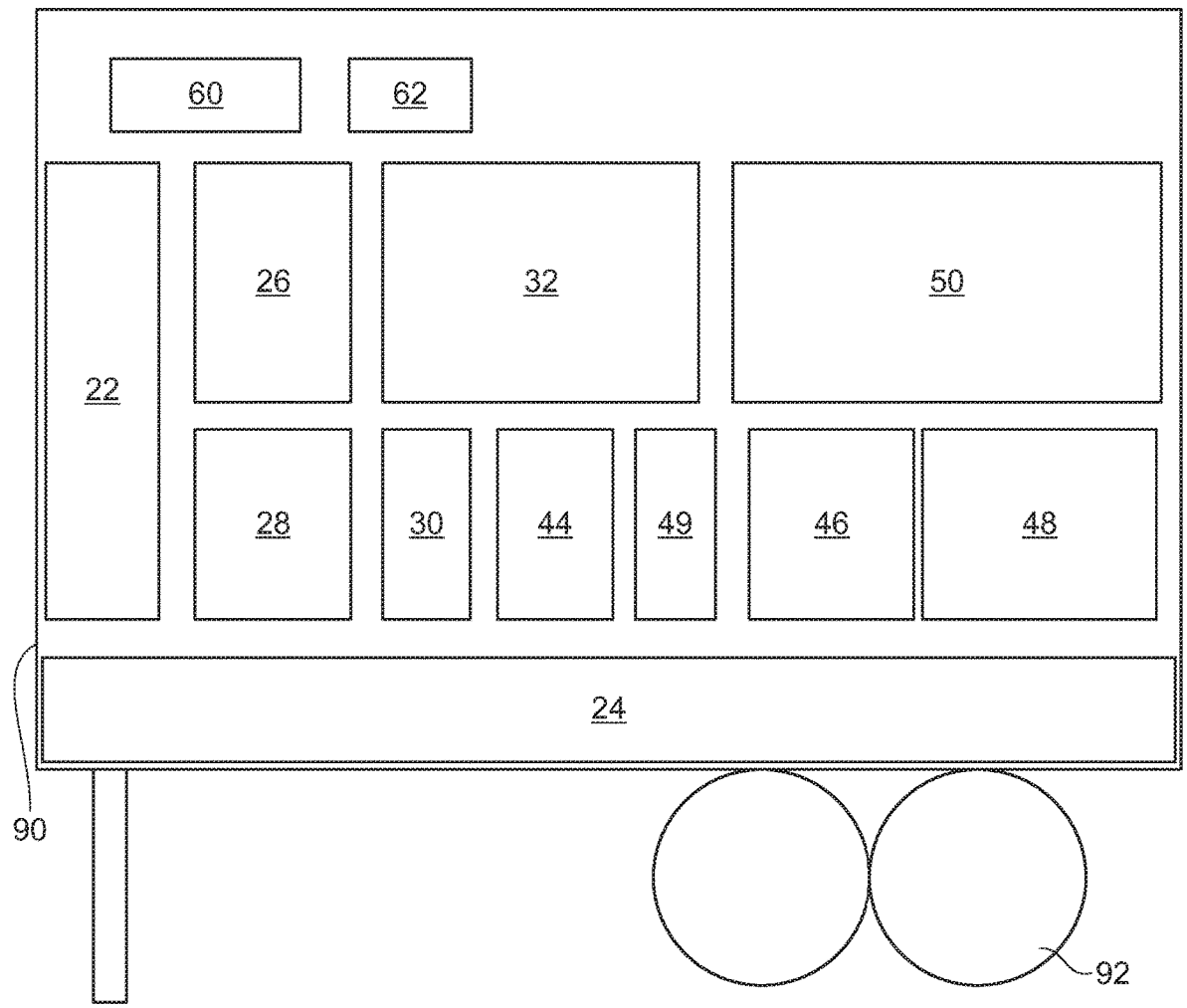
FIG. 4A is a is a stylized partial cutaway view of a portable enclosure with an arrangement of components comprising a software architecture and system for delivering selected sanitation protocols for multiple pathogens and pests in accordance with an example embodiment.
Figure 4B:
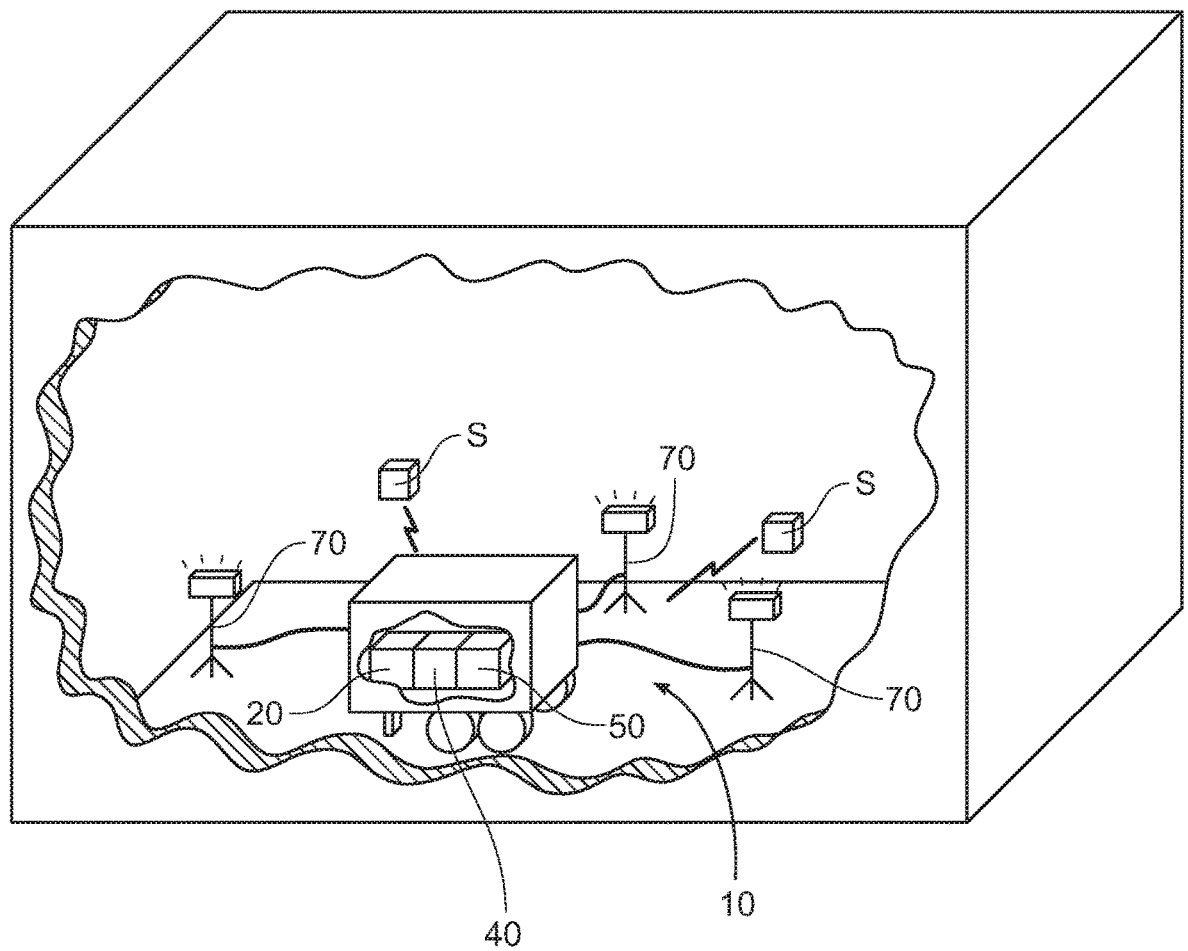
FIG. 4B is a stylized partial cutaway view of the portable enclosure of FIG. 4A illustrated with a controller, heat source, UV light source, and sensors comprising a software architecture and system for delivering selected sanitation protocols for multiple pathogens and pests coupled in a closed-loop feedback control arrangement in a physical space to be sanitized in accordance with an example embodiment.
Figure 5:
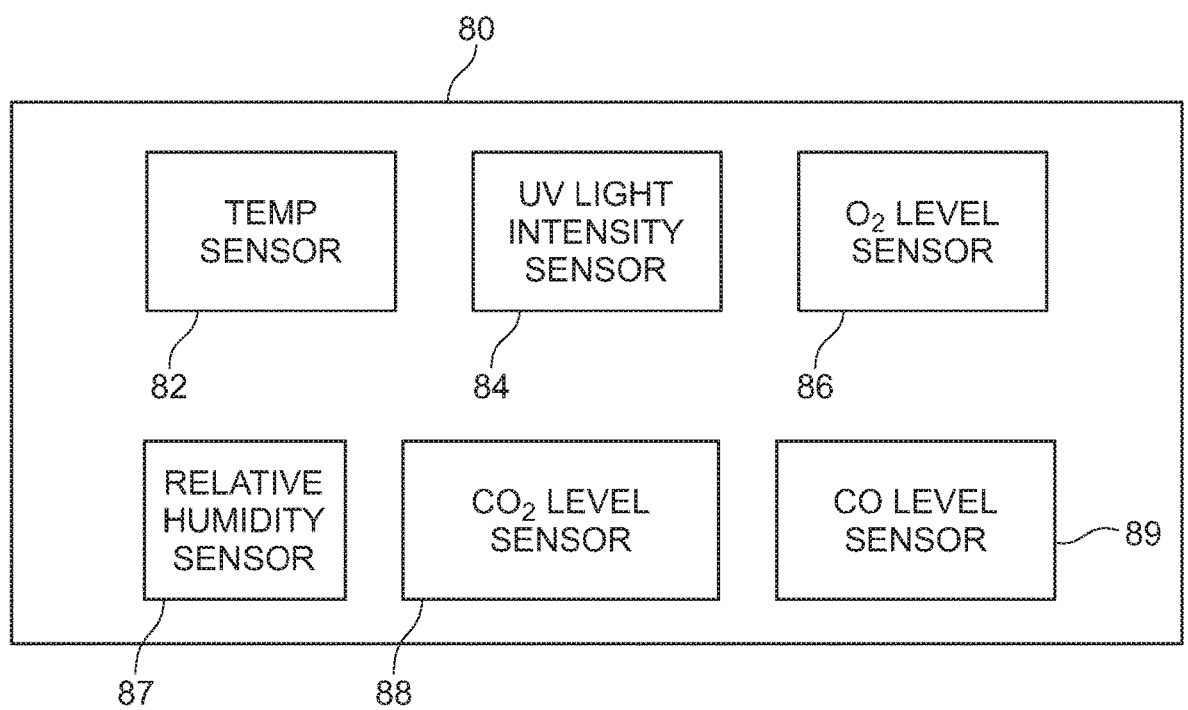
FIG. 5 is a block diagram illustrating telemetry and sensor components comprising a portion of a software architecture and system for delivering selected sanitation protocols for multiple pathogens and pests in accordance with an example embodiment.

A. Overview.

An example software architecture and system for delivering selected sanitation protocols for multiple pathogens and pests 10 generally includes a plurality of different sanitation protocols 65. Each sanitation protocol 65 is comprised of a plurality of different parameters, including protocol and operational parameters, for carrying out a plurality of different sanitation processes for a plurality of target pests and pathogens in a physical space or area. The plurality of sanitation protocols 65 are arranged as pages in a protocol storage 68. The plurality of parameters comprising each sanitation protocol 65 are arranged in a tabular form.

The example software architecture and system 10 also generally includes a fuel cell system 20, electrical power system 40, heat source 50, controller 60, control panel/display 62, UV light source 70, and telemetry and sensors 80. The telemetry and sensors 80 comprise one or more temperature sensors and UV light intensity sensors. The components of the software architecture and system 10 can be contained in or on a portable enclosure 90 which can be positioned in or near a physical space or area to be sanitized. The one or more temperature sensors and UV light intensity sensors can be positioned at one or more locations in the physical space or area.

The fuel cell system 20 generates hydrogen locally using a reformer 26 and generates electricity locally from the hydrogen using a fuel cell stack 32. The electricity is provided to the electrical system 40, which uses it to charge a DC power storage 44. The power system 40 provides operating power to the other components of the software architecture and system from the DC power storage 44 and a DC-AC converter 46.

A plurality of selectable protocol identifiers 64 are displayed on the control panel and display 62. Each protocol identifier 64 can be individually selected by an operator or user using a protocol selector 66. Each protocol identifier 64 comprises a link to a corresponding sanitation protocol 65 in the protocol storage 68. The controller 60 processes the link of a selected protocol identifier 64 to access the corresponding selected sanitation protocol 65 in the protocol storage 68 and retrieve the corresponding parameters. The controller 60 communicates with and controls the operation of the heat source 50, UV light source 70, and telemetry and sensors 80 in a closed-loop feedback control arrangement to automatically carry out a sanitation process in the physical space or area according to the parameters of the selected sanitation protocol 65 with little or no manual intervention or involvement by an operator required.

An external protocol/parameter upload unit 67 can be coupled to the protocol storage 68. The external protocol/parameter upload unit 67 comprises a user interface that presents templates or forms that can be used to enter new protocol identifiers 64, new sanitation protocols 65 and new parameters and values corresponding thereto, or to edit existing protocol identifiers 64, sanitation protocols 65, and parameters and values corresponding thereto. The external protocol/parameter upload unit 67 enables easy uploading and updating of protocol identifiers 64, sanitation protocols 65, and parameters and values corresponding thereto in the protocol storage 68 as new pests, pathogens, and treatment protocols are identified or discovered. Once the sanitation protocols 65 and corresponding parameters are uploaded to the protocol storage 68, no additional manual programming, reprogramming, monitoring or adjustment of the parameters are required by an operator or user to carry out a sanitation process in a physical space or area.

B. Exemplary Telecommunications Networks.

The software architecture and system for delivering selected sanitation protocols for multiple pathogens and pests 10 may be utilized upon any telecommunications network 12 capable of transmitting data including voice data and other types of electronic data. Examples of suitable telecommunications networks 12 for the software architecture and system 10 include but are not limited to global computer networks (e.g. Internet), wireless networks, cellular networks, satellite communications networks, cable communication networks (via a cable modem), microwave communications network, local area networks (LAN), wide area networks (WAN), campus area networks (CAN), metropolitan-area networks (MAN), and home area networks (HAN). The software architecture and system 10 may communicate via a single telecommunications network 12 or multiple telecommunications networks 12 concurrently. Various protocols may be utilized by the electronic devices for communications such as but not limited to HTTP, SMTP, FTP and WAP (Wireless Application Protocol). The software architecture and system 10 may be implemented upon various wireless networks such as but not limited to 3G, 4G, LTE, CDPD, CDMA, GSM, PDC, PHS, TDMA, FLEX, REFLEX, IDEN, TETRA, DECT, DATATAC, and MOBITEX. The software architecture and system 10 may also be utilized with online services and internet service providers.

The Internet is an exemplary telecommunications network 12 for the software architecture and system 10. The Internet is comprised of a global computer network having a plurality of computer systems around the world that are in communication with one another. Via the Internet, the computer systems are able to transmit various types of data between one another. The communications between the computer systems may be accomplished via various methods such as but not limited to wireless, Ethernet, cable, direct connection, telephone lines, and satellite.

C. Central Communication Unit.

A central communication unit 14 may be coupled to and in communication with the software architecture and system for delivering selected sanitation protocols for multiple pathogens and pests 10 via the telecommunications network 12. The central communication unit 14 may be comprised of any central communication site with which communications may be established. The central communication unit 14 may be comprised of one or more units comprising one or more of a server computer, cloud based computer, virtual computer, home computer or other computer system capable of receiving and transmitting data via IP networks and the telecommunication networks 12. As can be appreciated, a modem or other communication device may be required between each of the central communication units 14 and the corresponding telecommunication networks 12. The central communication unit 14 may be comprised of any electronic system capable of receiving and transmitting information (e.g. voice data, computer data, etc.).

D. Mobile Device.

A mobile device 16 may be coupled to and in communication with the software architecture and system for delivering selected sanitation protocols for multiple pathogens and pests 10 via the telecommunications network 12. The mobile device 16 may be comprised of any type of computer for practicing the various aspects of the software architecture and system 10. For example, the mobile device 16 can be a personal computer (e.g. APPLE® based computer, an IBM based computer, or compatible thereof) or tablet computer (e.g. IPAD®). The mobile device 16 may also be comprised of various other electronic devices capable of sending and receiving electronic data including but not limited to smartphones, mobile phones, telephones, personal digital assistants (PDAs), mobile electronic devices, handheld wireless devices, two-way radios, smart phones, communicators, video viewing units, television units, television receivers, cable television receivers, pagers, communication devices, and digital satellite receiver units.

The mobile device 16 may be comprised of any conventional computer. A conventional computer preferably includes a display screen (or monitor), a printer, a hard disk drive, a network interface, and a keyboard. A conventional computer also includes a microprocessor, a memory bus, random access memory (RAM), read only memory (ROM), a peripheral bus, and a keyboard controller. The microprocessor is a general-purpose digital processor that controls the operation of the computer. The microprocessor can be a single-chip processor or implemented with multiple components. Using instructions retrieved from memory, the microprocessor controls the reception and manipulations of input data and the output and display of data on output devices. The memory bus is utilized by the microprocessor to access the RAM and the ROM. RAM is used by microprocessor as a general storage area and as scratch-pad memory, and can also be used to store input data and processed data. ROM can be used to store instructions or program code followed by microprocessor as well as other data. A peripheral bus is used to access the input, output and storage devices used by the computer. In the described embodiments, these devices include a display screen, a printer device, a hard disk drive, and a network interface. A keyboard controller is used to receive input from the keyboard and send decoded symbols for each pressed key to microprocessor over bus. The keyboard is used by a user to input commands and other instructions to the computer system.

Other types of user input devices can also be used in conjunction with the software architecture and system 10. For example, pointing devices such as a computer mouse, a track ball, a stylus, or a tablet to manipulate a pointer on a screen of the computer system. The display screen is an output device that displays images of data provided by the microprocessor via the peripheral bus or provided by other components in the computer. The printer device when operating as a printer provides an image on a sheet of paper or a similar surface. The hard disk drive can be utilized to store various types of data. The microprocessor together with an operating system operate to execute computer code and produce and use data. The computer code and data may reside on RAM, ROM, or hard disk drive. The computer code and data can also reside on a removable program medium and loaded or installed onto computer system when needed. Removable program mediums include, for example, CD-ROM, PC-CARD, USB drives, floppy disk and magnetic tape. The network interface circuit is utilized to send and receive data over a network connected to other computer systems. An interface card or similar device and appropriate software implemented by microprocessor can be utilized to connect the computer system to an existing network and transfer data according to standard protocols.

E. Hydrogen Fuel Cell System.

The hydrogen fuel cell system 20 of the software architecture and system for delivering selected sanitation protocols for multiple pathogens and pests 10 comprises the main source of operating power for the other components of the software architecture and system 10. The use of the hydrogen fuel cell system 20 as the main power source enables the software architecture and system 10 to be mobile, self-contained, and to operate without requiring electrical connection to an outside source of electrical power, such as the AC electrical system of a physical facility or space, or a generator, in order to sanitize the physical facility or space according to a selected sanitation protocol 65.

The hydrogen fuel cell system 20 is adapted to locally generate hydrogen from a feedstock and to locally generate electrical power from the hydrogen. The electrical power generated by the hydrogen fuel cell system 20 is provided to and used to power the other components of the software architecture and system 10. These include, but are not limited to, an electrical power system 40, a heat source 50, a controller 60 and control panel/display 62, and an ultraviolet light (UV) source 70.

The electrical power generated by the hydrogen fuel cell system 20 also may be used to power other peripherals that may be incorporated as part of the software architecture and system 10 or that may be electrically connected thereto. These may include for example hard-wired sensors, aerosol dispensers, electronic filters, air distribution equipment, etc.

The hydrogen fuel cell system 20 is electrically coupled to the electrical power system 40 of the software architecture and system 10. The electrical power generated by the hydrogen fuel cell system 20 is processed and used by the electrical power system 40 as described further below to provide electrical power to the other components of the software architecture and system 10 as identified above. The hydrogen fuel system 20 is thus electrically coupled via the electrical power system 30 to the other components of the software architecture and system 10.

The hydrogen fuel cell system 20 preferably comprises a cooler 22, a fuel storage 24, a reformer 26, a hydrogen purifier 28, hydrogen storage 30, and one or more hydrogen fuel cells 32. The hydrogen fuel cell system 20 is adapted to carry out an electrochemical process to generate hydrogen locally and to convert the hydrogen to electricity locally.

The fuel storage 24 may comprise one or more tanks adapted to contain a volume of liquid fuel or feedstock from which hydrogen gas can be produced. The fuel storage 24 may comprise one or a plurality of tanks depending on the volume of fuel desired to be stored and the volume of hydrogen gas desired to be produced. It is preferred that the fuel storage 24 be of a size, volume, and weight to enable the software architecture and system 10 to be portable. The fuel storage 24 may be coupled to the reformer 26 by suitable plumbing.

The liquid fuel stored in the fuel storage 24 may comprise a suitable combination of methanol and deionized water. In this form, the fuel can be used to create hydrogen gas according to a well-known electrochemical process. Further, with proper maintenance this form of fuel presents little or no risk of fire or explosion, and poses little or no hazard to the environment in the event of an inadvertent leak, spill, or other release.

To minimize the risk of the fuel combusting, a cooler 22 is preferably provided. The cooler 22 is preferably adapted to chill the fuel in the fuel tanks 24 and to maintain the fuel at a temperature below about fifty degrees Fahrenheit ("F."). In this temperature range, the fuel is non-combustible since the vapor pressure is too low to ignite. A refrigerant-based cooler 22 may be used for this purpose if desired.

The reformer 26 is adapted to receive the liquid fuel from the fuel storage 24 via suitable plumbing and to produce hydrogen gas locally from the liquid fuel. The reformer 26 and the fuel storage 24 are preferably selected to be capable of producing a sufficient volume of hydrogen at a sufficient rate to enable the hydrogen fuel cell 32 to produce the electrical power necessary for the components and peripherals of the software architecture and system 10 to operate to sanitize a physical space or area of a facility according to a selected sanitation protocol.

Many forms of reformers and reformer processes are suitable for use as the reformer 26. For example, the reformer 26 may comprise an electrically-powered heater that can produce and apply sufficient heat to the liquid fuel to "crack" it to produce hydrogen gas. The heater may be powered by connecting it to an external source of electrical power or to the electrical power system 40 described further below.

The electrochemical process carried out by the reformer 26 may produce hydrogen gas that is less than pure and that is entrained with other gases and impurities. Accordingly, the reformer 26 is preferably coupled to a hydrogen purifier 28 via suitable plumbing. The hydrogen purifier 28 is adapted to receive the hydrogen gas from the reformer 26 via the plumbing and to produce purified hydrogen gas for use by the fuel cell 32. The hydrogen purifier 28 may comprise one or more suitable filters adapted to purify the hydrogen gas.

The purified hydrogen gas may be stored in a hydrogen storage 30. The hydrogen storage 30 may be coupled to the hydrogen purifier 28 by suitable plumbing. The hydrogen storage 30 is adapted to receive the purified hydrogen gas from the hydrogen purifier 28 via the plumbing and to store it under pressure for use on demand by the fuel cell 32. The hydrogen storage 30 may comprise one or more storage tanks. Preferably, the hydrogen storage 30 is adapted to store a sufficient volume of the purified hydrogen gas to enable the hydrogen fuel cell 32 to produce the electrical power necessary for the components and peripherals of the software architecture and system 10 to operate to sanitize a physical space or area of a facility according to a selected sanitation protocol 65. Also preferably, the hydrogen storage 30 is of a size, volume, and weight to enable the software architecture and system 10 to be portable.

In order to minimize the risk of accidents, the pressure of the purified hydrogen gas stored in the hydrogen storage 30 may be regulated. For that purpose, a hydrogen purge line and valve may be provided and connected to the hydrogen storage 30 via suitable plumbing. In the event the purified hydrogen gas stored in the hydrogen storage 30 exceeds a predetermined pressure limit or it is otherwise desired or necessary to purge hydrogen from the fuel cell system 20, the purge valve may be manually or remotely and automatically activated to release hydrogen gas from the hydrogen storage 30 and reduce the pressure to a desired level.

As an alternative to the cooler 22, liquid fuel storage 24, reformer 26, and hydrogen purifier 28, the hydrogen gas may be produced externally rather than locally. The externally-produced hydrogen gas may be transferred to the hydrogen storage 30 using suitable plumping and transfer equipment, e.g., pumps, or may be provided as compressed hydrogen gas in one or more tanks that may comprise or replace the hydrogen storage 30. However, in many instances the local storage of a relatively large volume of compressed hydrogen gas is undesirable and it will instead be preferred to produce the hydrogen gas locally in smaller volume and on an as-needed basis as described above.

The hydrogen storage 30 may be coupled to the hydrogen fuel cell 32 by suitable plumbing. If the hydrogen storage 30 comprises multiple storage tanks, the plumbing may include a suitable manifold system and/or one or more valves adapted to provide the hydrogen gas from the hydrogen storage 30 to the hydrogen fuel cell 32 on an as needed and on-demand basis.

The hydrogen fuel cell 32 is adapted to receive the purified hydrogen gas from the hydrogen storage 30 via the plumbing and to produce electricity locally from the hydrogen gas. Many hydrogen fuel cells are suitable for use as the hydrogen fuel cell 32. In one suitable form, the hydrogen fuel cell 32 electrochemically combines the hydrogen gas with atmospheric oxygen to directly produce electricity. The process produces as by-products heat and water. The heat may be allowed to radiate into the environment and dissipate. The water may be used for any purpose (with appropriate treatment to eliminate any contaminants that may be introduced after the fuel cell system), or may be discharged into a gray water/black water drain or collection system without harm.

Preferably, the hydrogen fuel cell 32 will be selected to produce sufficient electricity to enable the components and peripherals of the software architecture and system 10 to operate to sanitize a physical space or area of a facility according to a selected sanitation protocol 65. Also preferably, the hydrogen fuel cell 32 will be of a size and weight to enable the software architecture and system 10 to be portable. For these purposes, the hydrogen fuel cell 32 may comprise one or more units, which may be physically and electrically arranged and interconnected as one or more fuel cell stacks 32.

The components comprising the hydrogen fuel cell system 20 are preferably connected to and adapted to communicate with the controller 60 of the software architecture and system 10 via one or more suitable wired or wireless network or direct connections. The components comprising the hydrogen fuel cell system 20 are preferably adapted to communicate operational status and other information to the controller 60. The components comprising the hydrogen fuel cell system 20 also are preferably adapted to receive and respond to control commands from the controller 60 according to the operational parameters of a selected sanitation protocol 65. Such commands may include, for example, to activate and de-active the components to produce hydrogen gas, to activate and de-activate the components to produce electrical power or energy, and to control the operation of the components to control the level of electrical power output by the fuel cell system 20.

F. Electrical Power System.

The electrical power system 40 of the software architecture and system for delivering selected sanitation protocols for multiple pathogens and pests 10 is electrically coupled to the hydrogen fuel cell system 20 and to the other components and peripherals of the software architecture and system 10 by suitable electrical wiring and components. The electrical power system 40 is adapted to receive the electrical power generated by the hydrogen fuel cell system 20, process and store the electrical power, and convert the electrical power into a form suitable to energize and operate the other components and peripherals of the software architecture and system 10, including the heat source 50 and UV light source 70.

The electrical power system 40 preferably comprises a power conditioner and regulator 42, a DC power storage 44, and a DC-AC converter 46. The power conditioner and regulator 42 is electrically coupled to the fuel cell system 20 and to the DC power storage 44 by suitable electrical wiring and components. The power conditioner and regulator 42 is adapted to receive the electrical power generated by the hydrogen fuel cell system 20 and to process it into a form suitable for use by the DC power storage 44 and the other components and peripherals of the software architecture and system 10.

The power conditioner and regulator 42 may comprise suitable electrical circuitry adapted to rectify and filter the electrical power received from the hydrogen fuel cell system 20. The power conditioner and regulator 42 is adapted to provide the processed, e.g., rectified and filtered, electrical power to the DC power storage 44 for storage. The power conditioner and regulator 42 also may comprise electrical circuitry that is adapted to sense and regulate the level of electrical power stored in the DC power storage 44, for example by sensing voltage and current flow, and to charge or recharge the level of electrical power stored in a suitable manner and as necessary to maintain a predetermined or desired level.

The DC power storage 44 is electrically coupled to the power conditioner and regulator 42 and may also be electrically coupled to other components and peripherals of the software architecture and system 10 that may operate on DC power by suitable electrical wiring and components. The DC power storage 44 is adapted to receive the processed electrical power from the power conditioner and regulator 42, store the processed electrical power, and provide the stored electrical power to the components and peripherals of the software architecture and system 10 that operate on DC power as energizing and operating power, including for example the heat source 50 and/or the UV light source 70.

The DC power storage 44 may also be electrically coupled to one or more electrical outlets or sockets via suitable electrical wiring and components. The electrical power stored in the DC power storage 44 may thus be provided to and used to power peripherals external to the software architecture and system 10 that operate on DC power and that are electrically connected to such outlets or sockets.

The DC power storage 44 may comprise one or more batteries. If multiple batteries are employed, they may be arranged and electrically coupled as one or more battery banks.

The DC-AC converter 46 is electrically coupled to the DC power storage 44 and may also be electrically coupled to components and peripherals of the system 10 that may operate on AC power by suitable electrical wiring and components. The DC-AC converter 46 is adapted to receive the stored electrical power from the DC power storage 44 in a DC form and to convert it into an AC form for use by the components and peripherals of the system 10 that require operating power in the AC form, which may include the heat source 50 and/or the UV light source 70. The DC-AC converter 46 may comprise any suitable electronic circuitry for converting DC power to AC power.

The DC-AC converter 46 may also be electrically coupled to one or more electrical outlets or sockets via suitable electrical wiring and components. The AC electrical power generated by the DC-AC converter 46 may thus be provided to and used to power peripherals external to the software architecture and system 10 that operate on AC power and that are electrically connected to such outlets or sockets.

The components comprising the electrical power system 40 are preferably connected to and adapted to communicate with the controller 60 of the software architecture and system 10 via one or more suitable wired or wireless network or direct connections. The components comprising the electrical power system 40 are preferably adapted to communicate operational status and other information to the controller 60. The components comprising the electrical power system 40 also are preferably adapted to receive and respond to control commands from the controller 60 according to the operational parameters of a selected sanitation protocol 65. Such commands may include, for example, to activate and de-active the components to condition, regulate, store, and convert electrical power, to control the operation of the components to control the level of electrical power output, and to control to which components and peripherals the electrical power system 40 provides operating power.

G. Heat Source.

The heat source 50 of the software architecture and system for delivering selected sanitation protocols for multiple pathogens and pests 10 is electrically coupled to the electrical power system 30 via suitable electrical wiring and components. The heat source 50 is adapted to receive operating power from and to be powered by the electrical power system 30. The heat source 50 is coupled to and is adapted to be controlled by the controller 60. Under control of the controller 60, the heat source 50 is operable to produce and distribute heated air into a physical space or area to be sanitized in accordance with the protocol and operational parameters of a selected sanitation protocol 65.

The heat source 50 may comprise an AC-powered or a DC-powered heat source. The heat source 50 may comprise a single unit or a plurality of units. The units may be combined together in one or more enclosures or housings, such as a portable enclosure 90, or may be physically separate. Preferably, the heat source 50 comprises a heat pump. The heat source 50 also may comprise one or more air distributors, such as fans, blowers, or the like, which may be physically integrated with or may be physically separate from the preferred heat pump.

Under the control of the controller 60, the heat source 50 should be operable to produce heated air at a temperature sufficient to achieve a target temperature in the physical space or area being sanitized as specified by the protocol and operational parameters of a selected sanitation protocol 65. The heat source 50 also should be adapted to maintain the heated air at a temperature for a period of time sufficient to maintain the target temperature in the physical space or area for a dwell time as specified by the parameters of the selected sanitation protocol 65. The heat source 50 also should be adapted to ramp the temperature of the heated air either substantially continuously or in increments over a sufficient time to achieve a corresponding substantially continuously or discretely ramped temperature of the physical space or area being sanitized over a ramp time as specified by the parameters of the selected sanitation protocol 65.

The protocol parameters of the selectable sanitation protocols 65 that relate to heat and temperature may include various combinations of target temperature and dwell time depending on the target pathogens and/or pests to be treated, the nature, size, and contents of the physical space or area being sanitized, and other considerations. As just a few examples, a number of published peer-reviewed journal articles available via PubMed and the U.S. National Institutes of Health (NIH) (https://pubmed.ncbi.nlm.nih.gov/) have reported analyzing the effect of heat and exposure time on pathogens comprising at least two major coronavirus strains in the laboratory and finding that the virus was inactivated with various combinations of target heat and dwell or exposure time parameters as follows:

insects, in the physical space being sanitized at the same time. In that regard, it has been found that prolonged exposure to target temperatures between about 120° F. and 140° F. is effective to kill various insects from larval stages to mature adults. This is well within the range of target temperatures also found effective to inactivate various pathogens as set forth in Table 1.

Selectable sanitation protocols 65 that are to be employed to sanitize against pests as well as pathogens will preferably also include protocol and operational parameters for controlling the ramp rate of the temperature in the physical space or area to be sanitized. Controlling the temperature ramp rate is preferred because if the temperature is raised too quickly, pests may detect the rapid change of temperature as a threat, and may actively attempt to leave the area or space being heated. However, if the temperature ramp rate is more gradual, pests may instead detect the gradual rise in temperature as the introduction of a human, and move towards the heat source to feed, thus resulting in more complete eradication. Protocol parameters related to the temperature ramp rate may include for example, a combination of one or more of total ramp time, beginning temperature, ending temperature, which may correspond to the target temperature, a continuous ramp rate or slope (e.g., degrees per minute), one or more incremental or discrete ramp values (e.g., degrees per step), one or more incremental or discrete ramp times (e.g., 1 minute per step), as well as other parameters related to the ramp rate and time. Related operational parameters may include, for example, activate and deactivate the heat source 50 and/or an air distributor, change the heat setting of the heat source 50 and/or the operating speed of the air distributor, start and stop a timer, counter, or clock, and take readings from a timer, counter, or clock.

| TARGET TEMP | DWELL TIME | PATHOGEN/ PEST | SOURCE |
| --- | --- | --- | --- |
| 56° C./133° F. | Unspecified | SARS-CoV-1 | Henwood (2020) (https://pubmed.ncbi.nlm.nih.gov/32116147) |
| 56° C./133° F. | 25 minutes | MERS-CoV | Leclercq, et. al. (2014) (https://www.ncbi.nlm.nih.gov/pmc/articles/PMC4181824/) |
| 65° C./149° F. | 1 minute | MERS-CoV | Leclercq, et. al. (2014) (https://www.ncbi.nlm.nih.gov/pmc/articles/PMC4181824/) |
| 60° C./140° F. | 15-30 minutes | SARS-CoV-1 | Darnell & Taylor (2006) (https://pubmed.ncbi.nlm.nih.gov/17002634) |
| 56° C./133° | 60 minutes | SARS-CoV-1 | Kariwa, et. al. (2006) (https://pubmed.ncbi.nlm.nih.gov/16490989) |
| 56° C./133° F. | Unspecified | SARS-CoV-1 | Rabenau, et. al. (2005) (https://www.ncbi.nlm.nih.gov/pmc/articles/PMC7086689/) |
| 60° C./140° F. | 30 minutes | SARS-CoV-1 | Rabenau, et. al. (2005) (https://www.ncbi.nlm.nih.gov/pmc/articles/PMC7086689/) |
| 65° C./149° F. | Unspecified | SARS-CoV-1 | Darnell, et. al. (2004) (https://pubmed.ncbi.nlm.nih.gov/15350737) |
| 60° C./140° F. | 30 minutes | SARS-CoV-1 | Yunoki, et. al. (2004) (https://pubmed.ncbi.nlm.nih.gov/15585028) |
| 55° C./131° F. | Unspecified | SARS-CoV-1 | Wang, et. al. (2004) (https://pubmed.ncbi.nlm.nih.gov/15323569) |
| 75° C./167° F. | 30 minutes | SARS-CoV-1 | Duan, et. al. (2003) (https://pubmed.ncbi.nlm.nih.gov/14631830) |
| 67° C./153° F. | 60 minutes | SARS-CoV-1 | Duan, et. al. (2003) (https://pubmed.ncbi.nlm.nih.gov/14631830) |
| 56° C./133° F. | 90 minutes | SARS-CoV-1 | Duan, et. al. (2003) (https://pubmed.ncbi.nlm.nih.gov/14631830) |

Preferably, at least some selectable sanitation protocols 65 will comprise heat and temperature-related protocol parameters that are effective to inactivate a target pathogen or group of target pathogens and to kill one or more target pests or target groups of pests, such as one or more types of The components comprising the heat source 50 are preferably connected to and adapted to communicate with the controller 60 via one or more suitable wired or wireless network or direct connections. The components comprising the heat source 50 preferably are adapted to communicate operational status and other information to the controller 60. The components comprising the heat source 50 also are preferably adapted to receive and respond to control commands from the controller 60 according to the protocol and operational parameters of a selected sanitation protocol 65. With respect to protocol parameters, such commands may include, for example, a temperature setting at which the air is to be heated, and/or an air distributor speed setting, as well as the ramp-related protocol parameters described above. With respect to operational parameters, such commands may include, for example, commands to activate and deactivate, increase and decrease temperature, as well as the ramp-related operational parameters described above.

It will be appreciated that if the heat source 50 includes an integrated air distributor, the operation of the heat source 50 and the air distributor may be controlled by the controller 60 together according to parameters of the selected sanitation protocol 65. Alternatively, if a separate air distributor is included, the operation of the heat source 50 and the air distributor may be controlled by the controller 60 separately according to separate parameters of a selected sanitation protocol 65.

H. UV Light Source.

The UV light source 70 of the software architecture and system for delivering selected sanitation protocols for multiple pathogens and pests 10 is electrically coupled to the electrical power system 30 via suitable electrical wiring and components. The UV light source 70 is adapted to receive operating power from and to be powered by the electrical power system 30. The UV light source 70 is coupled to and is adapted to be controlled by the controller 60. Under control of the controller 60, the UV light source is operable to produce UV radiation to irradiate all or a portion of the physical space or area to be sanitized in accordance with the protocol and operational parameters of a selected sanitation protocol 65.

The UV light source 70 may comprise an AC-powered or a DC-powered source. The UV light source 70 may comprise a single unit or a plurality of units. The units may be combined together in one or more enclosures or housings or may be physically separate. It will be appreciated that a plurality of physically separate UV light sources 70 may be positioned and spaced apart in a physical space or area to be sanitized so as to irradiate all or selected portions thereof.

The UV radiation produced by the UV light source 70 is preferably capable of reducing or eradicating various microorganisms in the physical space or area to be sanitized, including potentially one or more pathogens, and more preferably one or more of the viruses identified in Table 1. In addition, the UV radiation produced by the UV light source 70 is preferably capable of reducing or eliminating one or more allergens and undesirable odors in the physical space or area being sanitized.

The use of UV light, such as (but not limited to) UVC, has been found to be capable of killing a variety of microorganisms. Accordingly, positioning one or more UV light sources 70 in a physical space or area to be sanitized, in combination with applying heat to the physical space or area as described herein, provides a particularly effective way to reduce or eradicate pathogens and other microorganisms in the physical space, including pathogens and other microorganisms that may be resistant to eradication from heat alone.

The use of UVC for sterilization has been found to be particularly effective. The United States Department of Health and Human Services (HHS) has reported that UVC treatment is equally effective to multidrug-resistant microorganisms as to treatment of wild-type microorganisms that are not resistant to chemical treatments. UVC spans the ultraviolet spectrum from 200-280 nm, with 262 nm being the peak germicidal wavelength. Thus, UV light sources that irradiate in the UVC spectrum are preferred.

Preferably one or more of the protocol and operational parameters of one or more selectable sanitation protocols 65 will include parameters for controlling the UV light source 70 to irradiate all or a portion of the physical space or area to be sanitized. One or more protocol parameters may include, for example, one or more of radiation band selection (e.g., UVC), radiation output intensity (e.g., $mW/cm^2$), and exposure time. One or more operational parameters may include, for example, activate, de-activate, and increase or decrease output intensity.

The UV light source 70 is preferably connected to and adapted to communicate with the controller 60 via one or more suitable wired or wireless network or direct connections. The UV light source 70 preferably is adapted to communicate operational status and other information to the controller 60. The UV light source 70 is also preferably adapted to receive and respond to control commands from the controller 60 according to the protocol and operational parameters of a selected sanitation protocol 65, such as commands related to the protocol and operational parameters described above.

I. Telemetry and Sensors.

The telemetry and sensors 80 of the software architecture and system for delivering selected sanitation protocols for multiple pathogens and pests 10 may comprise one or more telemetry devices and/or sensors adapted to detect, sense, and/or measure physical conditions in the physical space or area being sanitized. The telemetry and sensors 80 are adapted to communicate data concerning the physical conditions to the software architecture and system 10 via one or more suitable wired or wireless network or direct connections.

The telemetry and sensors 80 may be self-powered, for example via batteries, or may be electrically coupled to the electrical power system 30 via suitable electrical wiring and components and adapted to be powered by the electrical power system 30. In the latter case, the telemetry and sensors 80 may be DC-powered or AC-powered.

More particularly, the telemetry devices and/or sensors comprising the telemetry and sensors 80 are preferably connected to and adapted to communicate with the controller 60 via one or more suitable wired or wireless network or direct connections. The telemetry and sensors 80 preferably are adapted to communicate data indicative of various physical conditions in the physical space or area being sanitized to the controller 60. The telemetry and sensors 80 may be adapted to communicate such data continuously or upon demand. The telemetry and sensors 80 may be adapted to receive and respond to control commands from the controller 60, including for example commands to set a sensitivity level, set filtering values for measurements, take measurements or readings of one or more physical conditions, and communicate data indicative of the conditions to the controller 60.

The telemetry and sensors 80 may comprise numerous different types of telemetry devices and sensors, including for example temperature sensors 82, UV radiation intensity sensors 84, oxygen ($O_2$) sensors 86, relative humidity sensors 87, carbon dioxide ($CO_2$) sensors 88, and carbon monoxide (CO) sensors 89. Any combination of such telemetry devices and sensors may be included as part of the system 10, and one or more than one of the same type of sensor may be included.

One or more telemetry devices and/or sensors comprising the telemetry and sensors 80 may be positioned and spaced apart as desired in the physical space or area to be sanitized. Alternatively or in addition, one or more of the telemetry devices and sensors may be arranged on or in an enclosure or enclosures containing or supporting other components of the software architecture and system 10, for example a portable enclosure 90 described further below.

The telemetry and sensors 80 may comprise one or more telemetry devices located and spaced apart between the sensors and the controller 60 in or near the physical space or area to be sanitized. The telemetry devices may be in communication with the controller 60 via one or more suitable wired or wireless network or direct connections. The telemetry devices are preferably adapted to communicate wirelessly with and to receive data from one or more of the sensors in the physical space, and to communicate the data to the controller 60. The telemetry devices may include their own sensors or the sensors may incorporate their own telemetry devices.

The software architecture and system 10, including the controller 60 and the telemetry and sensors 80, is configured and is operable in a closed-loop feedback control arrangement to automatically carry out a sanitation process in a physical space or area to be sanitized according to the parameters of a selected sanitation protocol 65 with little or no manual intervention or involvement. More specifically, the components of the software architecture and system 10, for example the heat source 50 and UV light source 70, are automatically controlled by the controller 60 to operate to produce heat and UV radiation in the physical space or area according to the parameters of a selected sanitation protocol 65. The telemetry and sensors 80 are adapted to detect, sense, and/or measure physical conditions in the physical space, such as the temperature and the intensity of UV radiation, and to communicate data indicative of the physical conditions back to the software architecture and system 10, and more specifically the controller 60, with no manual intervention or involvement. The software architecture and system 10 and more specifically the controller 60 is adapted and configured to receive the data without any manual involvement, and to automatically respond to control the components, e.g., the heat source 50 and UV light source 70, according to corresponding parameters of the selected sanitation protocol 65 to automatically carry out the sanitation process specified by the selected sanitation protocol 65.

As one specific example of the automatic closed-loop feedback control arrangement, the software architecture and system 10 may receive data from the telemetry and sensors 80 indicating a temperature in the physical space that is below the target temperature specified in the selected sanitation protocol 65. In response, the software architecture and system 10 may control the heat source 50 to increase the temperature to the target temperature parameter specified by the selected sanitation protocol 65. As another specific example, the telemetry and sensors 80 may sense and communicate to the software architecture and system 10 data indicative of the temperature in the physical space over a period of time. The software architecture and system 10 may receive the data, process it, and determine that the temperature is ramping at a rate that is higher or lower than specified in the selected sanitation protocol 65. In response, the software architecture and system 10 may control the heat source 50 to increase or decrease the temperature over one or more periods of time to ramp the temperature as specified in the selected sanitation protocol 65. As yet another specific example, the software architecture and system 10 may receive data from the telemetry and sensors 80 indicating the intensity of the UV radiation produced by the UV light source 70 is greater or less than the intensity specified in the selected sanitation protocol 65. In response, the software architecture and system 10 may control the UV radiation source 70 to decrease or increase the intensity in accordance with the value specified by the selected sanitation protocol 65. Many other examples of a closed-loop control arrangement comprised of the components of the software architecture and system 10 and the telemetry and sensors 80 are possible and the foregoing specific examples are in no way to be construed as limiting.

J. Software Architecture and Storage for Selectable Sanitation Protocols.

The software architecture and system for delivering selected sanitation protocols for multiple pathogens and pests 10 comprises a plurality of selectable sanitation protocols 65, a protocol storage 68 adapted to receive, retain, and store the plurality of sanitation protocols 65, and a plurality of selectable protocol identifiers 64 adapted to enable selection by an operator or use of a corresponding sanitation protocol 65 in the protocol storage 68. Each sanitation protocol 65 comprises a plurality of parameters for carrying out a sanitation process in a physical space or area using the components of the software architecture and system 10 as described above. Preferably, the parameters corresponding to each sanitation protocol 65 comprise substantially all of the protocol parameters and operational parameters necessary for the controller 60 to control the components of the software architecture and system 10 to automatically carry out a sanitation process without any substantial manual intervention or involvement by an operator or user.

The protocol storage 68 may comprise any suitable storage device. Examples include non-volatile semiconductor memory, such as EPROM, magnetic disk storage, solid state disk storage, etc. The protocol identifiers 64 may comprise strings of alphanumeric text, graphical images, and/or or any other information or data suitable and adapted to uniquely identify each of a plurality of selectable sanitation protocols 65 to an operator or user. Preferably each protocol identifier 64 will comprise information from which a target pathogen, target group of pathogens, target pest, or target group of pests may be readily identified. Each protocol identifier 64 comprises a link to a corresponding sanitation protocol 65 in the protocol storage 68.

The sanitation protocols 65 stored in the protocol storage 68 are preferably arranged as a plurality of logical pages in the addressable space of the protocol storage 68 with each logical page comprising a sanitation protocol 65 and each sanitation protocol 65 comprising a plurality of fields of fixed or variable size. Each field may comprise one or more addressable locations of the addressable space. The logical pages also may be of fixed or variable size. Each sanitation protocol 65 has a unique starting address and a unique ending address in the addressable space of the protocol storage 68.

Figures 7, 8:
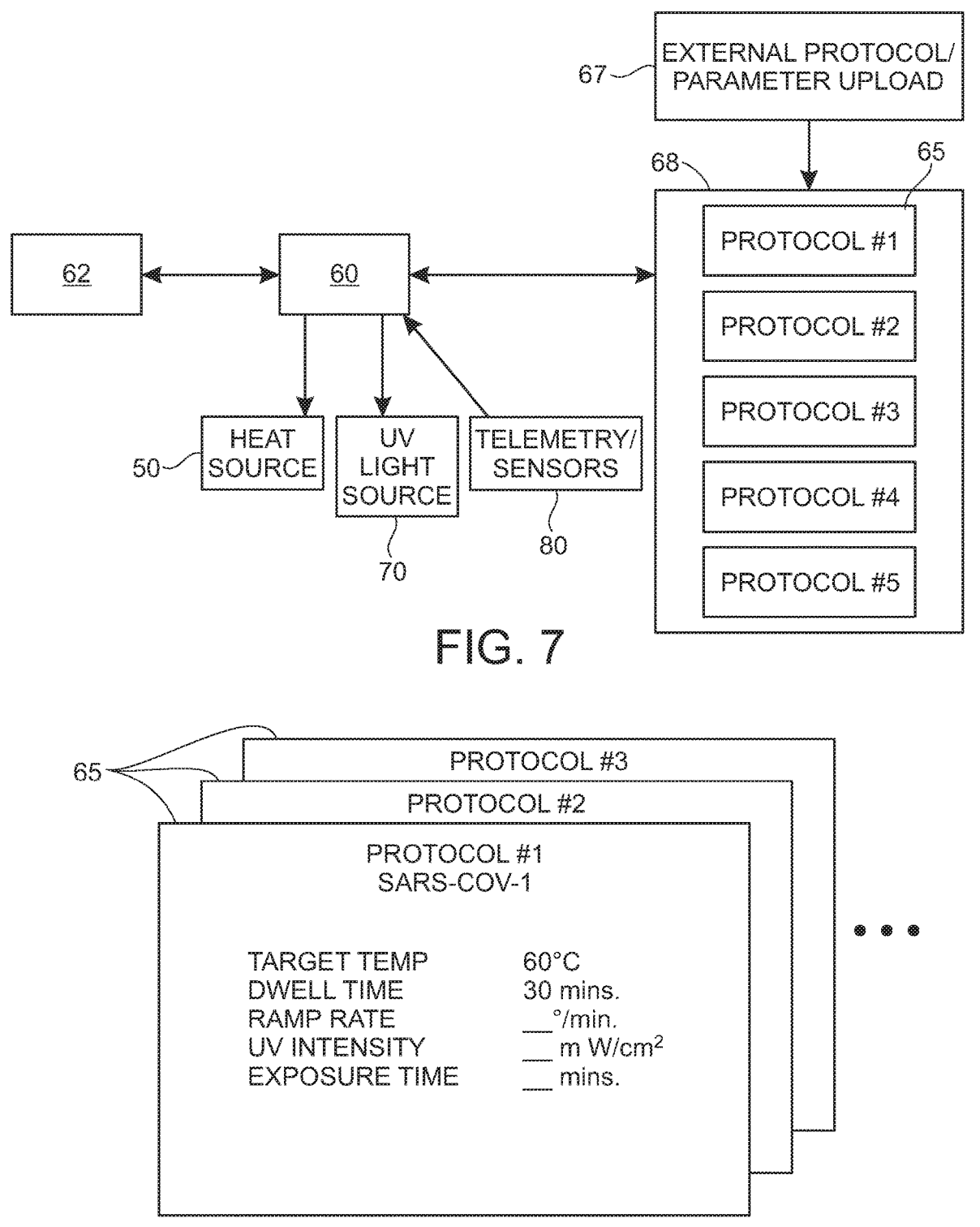

Each field of a sanitation protocol may comprise a parameter of the sanitation protocol 65, e.g., a protocol parameter or an operational parameter. Alternatively, one or more fields may be adapted to comprise multiple parameters, for example multiple related or dependent protocol and/or operational parameters. Preferably the fields and parameters are arranged in a logical tabular arrangement for example similar to the tabular arrangement illustrated in FIG. 8. Fields may also comprise data and values related to one or more parameters. For example, one field in a logical row or column of the logical tabular arrangement may include a descriptor of a protocol parameter such as "target temp" and the next field in the logical row may include the value of the "target temp." The order of successive fields in a logical row or column could implicitly indicate the order in which the parameters and/or values contained in the fields are to be applied by the controller 60. Alternatively, other means, such as an order of execution field in each logical row or column, could indicate the order in which the parameters in the fields of the row or column are to be applied. Of course, it will be appreciated that many other variations of the fields comprising the parameters and parameter values of the sanitation protocols 65 and related information are also possible.

Each protocol identifier 64 preferably comprises a unique link to a corresponding sanitation protocol 65. The link may comprise at least in part the unique starting address of the corresponding sanitation protocol 65 in the protocol storage 68. Alternatively or in addition, it may include a link to a remote location of the sanitation protocol 65 in the protocol storage 68, such as an https or ftp link to a remote location, for example a location at the central communication unit 14. Thus, selecting a protocol identifier 64 comprises selecting a corresponding sanitation protocol 65 in the protocol storage 68.

Many other storage arrangements for the sanitation protocols 65 and linkage arrangements with the protocol identifiers 64 are also possible. For example, in one alternative arrangement all of the stored sanitation protocols 65 may share a common addressable space in the protocol storage 68 with only the starting address of the common addressable space being fixed and the starting and ending addresses of each sanitation protocol 65 being non-fixed and variable. The sanitation protocols 65 may be arranged within the addressable space consecutively or in a linked or chained manner. The beginning of each sanitation protocol 65 within the addressable space may be signified by a unique header that comprises the protocol identifier 64 corresponding to the sanitation protocol 65. In response to selection of a protocol identifier 64, the external protocol/parameter upload unit 67 and/or the controller 60 may be configured to search the sanitation protocols 65 starting at the fixed starting address of the addressable space of the protocol storage 68 to locate a header that comprises a match for the selected protocol identifier 64. The search may continue through the successively-stored sanitation protocols 65 or by following the linked chain of sanitation protocols 65 until a sanitation protocol 65 with a header matching the selected protocol identifier 64 is located. That sanitation protocol 65 is the selected sanitation protocol 65.

In another alternative arrangement, a protocol identifier 64 may be linked to a corresponding sanitation protocol 65 by comprising an address offset from the fixed starting address of the addressable space of the protocol storage 68. The external protocol/parameter upload unit 67 and/or the controller 60 may be configured to determine the starting address of the corresponding stored sanitation protocol 65 from the fixed starting address and the offset.

Similar to a header at the beginning of a stored sanitation protocol 65, the end of a stored sanitation protocol 65 may be reflected by an indicator. The indicator may be as simple as a text string, e.g., "END." The external protocol/parameter upload unit 67 and/or the controller 60 may be configured to recognize the meaning of the indicator and to respond accordingly. For example, the external protocol/parameter upload unit 67 and/or the controller 60 may be configured to treat the next location of the addressable space of the protocol storage 68 after the indicator as the beginning of the next stored sanitation protocol 65, i.e., the sanitation protocols 65 may be stored independently in a consecutive arrangement.

Alternatively, the last location or locations of a stored sanitation protocol 65 may comprise, either alone or in combination with an indicator as described above, an address or a link to an address corresponding to the beginning of the next stored sanitation protocol 65. The external protocol/parameter upload unit 67 and/or the controller 60 may be configured to recognize the address or link, with or without the indicator, and to respond by processing it to determine the beginning of the next stored sanitation protocol 65, i.e., the sanitation protocols 65 may be stored in a linked chain arrangement. It will be further appreciated that the linked chain arrangement of the stored sanitation protocols 65 can be made one-way, as described above, or two-way by including in the first addressable location or locations of a stored sanitation protocol 65 the address corresponding to the beginning of the previous sanitation protocol 65 in the chain.

Each of the plurality of sanitation protocols 65 and the parameters and values thereof stored in the protocol storage 68 are selectable, accessible, retrievable, and updateable via its corresponding linked protocol identifier 64. Briefly, the plurality of protocol identifiers 64 corresponding to the stored sanitation protocols 65 may be displayed on a display of the control panel and display 62 and/or the external protocol/parameter upload unit 67. An operator or user may select a displayed protocol identifier 64 using a suitable input device. The controller 60 is coupled to and in communication with the control panel and display 62 and/or the external protocol/parameter upload unit 67. The controller 60 receives the selection of the protocol identifier 64, processes the link to determine the beginning address of the corresponding sanitation protocol 65 in the protocol storage 68, and accesses the contents of selected sanitation protocol 65. The controller 60 may read and retrieve some or all of the contents of the selected sanitation protocol 65 including one or more of the parameters and parameter values, for example to carry out a sanitation process according to the parameters. The controller 60 may overwrite all or part of the contents including one or more of the parameters, for example to update the sanitation protocol 65. If the selected protocol identifier 64 does not correspond to an existing sanitation protocol 65 in the protocol storage 68, the controller 64 or the external protocol/parameter upload unit 67 may write the new sanitation protocol 65 into the protocol storage 68 for future access. As part of the process of accessing, retrieving, updating, or writing the selected sanitation protocol 65 in the protocol storage 68, the controller 60 or external protocol/parameter upload unit 67 also updates the address or other link information of the protocol identifier 64 and any addresses or other links between the selected sanitation protocol 65 and the other sanitation protocols 65 in the protocol storage 68.

K. Controller.

The controller 60 of the software architecture and system for delivering selected sanitation protocols for multiple pathogens and pests 10 may be comprised of any type of computer, processor, electronic controller, or other electronic logic and/or software for practicing the various aspects of the software architecture and system 10. For example, the controller 60 can be a personal computer (e.g. APPLE® based computer, an IBM based computer, or compatible thereof) or tablet computer (e.g. IPAD®). The controller 60 may also be comprised of various other electronic devices capable of sending and receiving electronic data including but not limited to smartphones, mobile phones, telephones, personal digital assistants (PDAs), mobile electronic devices, handheld wireless devices, two-way radios, smart phones, communicators, video viewing units, television units, television receivers, cable television receivers, pagers, communication devices, and digital satellite receiver units. Further, the controller 60 may comprise one or more processors, microcontrollers, digital, analog, or mixed circuits, software, firmware, and internal or external configuration elements, such as programming, code, macros, and the like. Still further, the controller 60 may comprise data storage such as a magnetic disk or tape, optical media, or a solid-state storage device.

The controller 60 is electrically coupled to the electrical power system 40 and more particularly the DC power storage 44 via suitable electrical wiring and components. The controller 60 is adapted to receive and to be powered by the electrical power system 40 from the DC power storage 44.

The controller 60 is connected to and configured to communicate with the components of the software architecture and system 10 via suitable wired or wireless network or direct connections. These components include the components of the hydrogen fuel cell system 20, the components of the electrical power system 40, the heat source 50, a control panel and display 62, the external protocol/parameter upload unit 67, the UV light source 70, and the telemetry/sensors 80.

The controller 60 is adapted and configured to monitor the operational status of the foregoing components, and to receive operational status and other information from the foregoing components. The controller 60 is also adapted and configured to monitor and to receive data from the telemetry/sensors 80 indicative of one or more physical conditions in the physical space or area being sanitized according to a selected sanitation protocol 65. The controller 60 may be configured to obtain information and data from the foregoing components continuously, upon request, or at periodic intervals.

As examples, the status, information, and data may include such items as the volume and temperature of the fuel storage 24, the rate of usage of the fuel in the fuel storage 24, the level and/or pressure of the hydrogen in the hydrogen storage 30, the rate of hydrogen usage by the fuel cell stacks 32, the level of the electrical power generated by the fuel cell stacks 32, the voltage level of the DC power storage 44, the rate and level of charge and discharge of the DC power storage 44, the level of electrical current output from the DC power storage 44 and/or the DC-AC converter 46, the activation-deactivation state and temperature setting of the heat source 50, the temperature of the heated air at one or more locations in the physical space or area being sanitized, the activation/de-activation state UV intensity setting of the UV light source 70, an amount of time during which the heat source 50 has operated to heat the air to a particular temperature, and/or an amount of time during which the UV light source 70 has operated to generate UV radiation at a particular intensity. The information and data may also include such other items as the $O_2$ level, relative humidity level, $CO_2$ level, and/or CO level at one or more locations in the physical space or area being sanitized.

The controller 60 is also adapted and configured to control the foregoing components of the software architecture and system 10 by sending control commands in order to carry out a sanitation process in a physical space or area to be sanitized according to the protocol and operational parameters of a selected sanitation protocol 65. In addition to the example of commands described above with respect to the various components, control commands may include commands to activate and deactivate the cooler 22, set the cooling temperature of the cooler 22, activate and deactivate the reformer 26, activate and deactivate the fuel cell stacks 32, control the rate of operation of the reformer 26 and/or the fuel cell stacks 32, control the rate and level of charge and discharge of the DC power storage 44, cause a control panel and display 62 to display information, obtain the identity of a selected sanitation protocol from the control panel and display 62, retrieve stored parameters of a selected sanitation protocol 65 from a protocol storage 68, activate and deactivate the heat source 50, set the temperature of the heat source 50, activate and deactivate the UV light source 70, set the output intensity of the UV light source 70, request data from the telemetry and sensors 80, and others.

As described above, the controller 60 is connected and configured to operate with the components of the software architecture and system 10 and the telemetry and sensors 80 in a closed-loop feedback control arrangement adapted to automatically carry out a sanitation process in a physical space or area to be sanitized according to a selected sanitation protocol 65 substantially without manual intervention. More specifically, the controller 60 is configured to automatically control the operation of the components of the software architecture and system 10, for example the heat source 50 and UV light source 70, to produce heat and UV radiation in the physical space or area to be sanitized according to the parameters of the selected sanitation protocol 65. The controller 60 is configured and adapted to receive data indicative of physical conditions in the physical space, such as the temperature and the intensity of UV radiation, from the telemetry and sensors 80 without manual involvement. The controller 60 is configured to automatically respond to the data by sending control commands to control the components, e.g., the heat source 50 and UV light source 70, according to the corresponding parameters of the selected sanitation protocol 65 to automatically carry out the sanitation process specified by the selected sanitation protocol 65 substantially without manual involvement or intervention.

The controller 60 may be configured to log data about the operational status of the components and/or data received from the telemetry and sensors 80. The logged data may be stored locally in a local storage or remotely in a remote storage via the telecommunications network 12 or other network or direct connection. The controller 60 may be configured to use the logged data for numerous purposes. For example, the controller 60 may be configured to use the data to determine if the ramp rate of the temperature in the physical space or area being sanitized is correctly corresponds to the ramp rate parameter of a selected sanitation protocol 65, and if not to control the heat source 50 to adjust the ramp rate accordingly. The controller 60 may also be configured to use the data to determine if the temperature in the physical space corresponds to the target temperature parameter of a selected sanitation protocol 65, and if not control the heat source 50 to adjust the temperature accordingly. The controller 60 may also be configured to use the data to determine if the UV light intensity in the physical space corresponds to the intensity parameter of a selected sanitation protocol 65, and if not control the UV light source 70 to adjust the intensity accordingly.

The controller 60 is preferably coupled and in communication with the control panel and display 62, which is described further below, and with the sanitation protocol storage 68. The controller 60 may be coupled with the control panel and display 62 and/or with the sanitation protocol storage 68 via one or more suitable wired or wireless network or direct connections including for example the telecommunications network 12. The controller 60, the control panel/display 62, and the protocol storage 68 may comprise separate physical components or units, may be integrated as a single component or unit, and may be contained in a single or multiple enclosures. The controller 60, control panel/display 62, and protocol storage 68 may be located locally with respect to each other or remotely from each other. For example, in one example embodiment, one or more of the controller 60, control panel/display 62, and protocol storage 68 may be disposed locally with respect to each other in or on the portable enclosure 90. In another example embodiment, one or more of the controller 60, control panel/display 62, and protocol storage 68, may comprise part of the mobile device 16 or another device and be located remotely with respect to each other.

The controller 60 is adapted and configured to communicate with, send data to, and receive data from the control panel/display 62 and the protocol storage 68. For example, the controller 60 may be configured to send data to the control panel/display 62 to display protocol identifiers 64 identifying and linked to one or more selectable sanitation protocols 65 stored in the protocol storage 68. The controller 60 also may be configured to receive data from the control panel/display 62 indicative of a selection of a sanitation protocol 65. The controller 60 also may be configured to respond to that data by communicating with the protocol storage 68 and requesting and receiving the stored parameters comprising or corresponding to the selected sanitation protocol 65. The controller 60 also may be configured in response to control the other components of the software architecture and system 10 to automatically carry out a sanitation process according to the retrieved parameters of the selected sanitation protocol 65 as described herein. The controller 60 also may be configured to send data to the control panel display 62 to display the status of the sanitation process and/or the operational status of one or more components of the software architecture and system 10 and/or one or more conditions in the physical space or area being sanitized.

L. Control Panel/Display.

The control panel and display 62 provides a user interface to the software architecture and system for delivering selected sanitation protocols for multiple pathogens and pests 10. The control panel and display 62 may be coupled to the electrical power system 40 by suitable electrical wiring and components and be adapted to receive power from and to be powered by the electrical power system 40. Alternatively, the control panel and display 62 need not be coupled to the electrical power system 40 and may be self-powered, for example by a battery.

The control panel and display 62 is coupled to the controller 60 and is adapted to communicate data, information, and commands to the controller 60 and to receive data, information, and commands from the controller 60. The control panel and display 62 may be coupled to the controller 60 via one or more suitable wired or wireless network or direct connections. The control panel and display 62 may be comprised of the mobile device 16 and may communicate with the controller 60 over the telecommunications network 12.

The control panel and display 62 preferably comprises a display screen that is adapted to display data, information, and/or choices. The display screen may comprise any suitable user viewable display screen including for example a computer display screen or a display screen of a mobile device such as mobile device 16.

Figure 6:
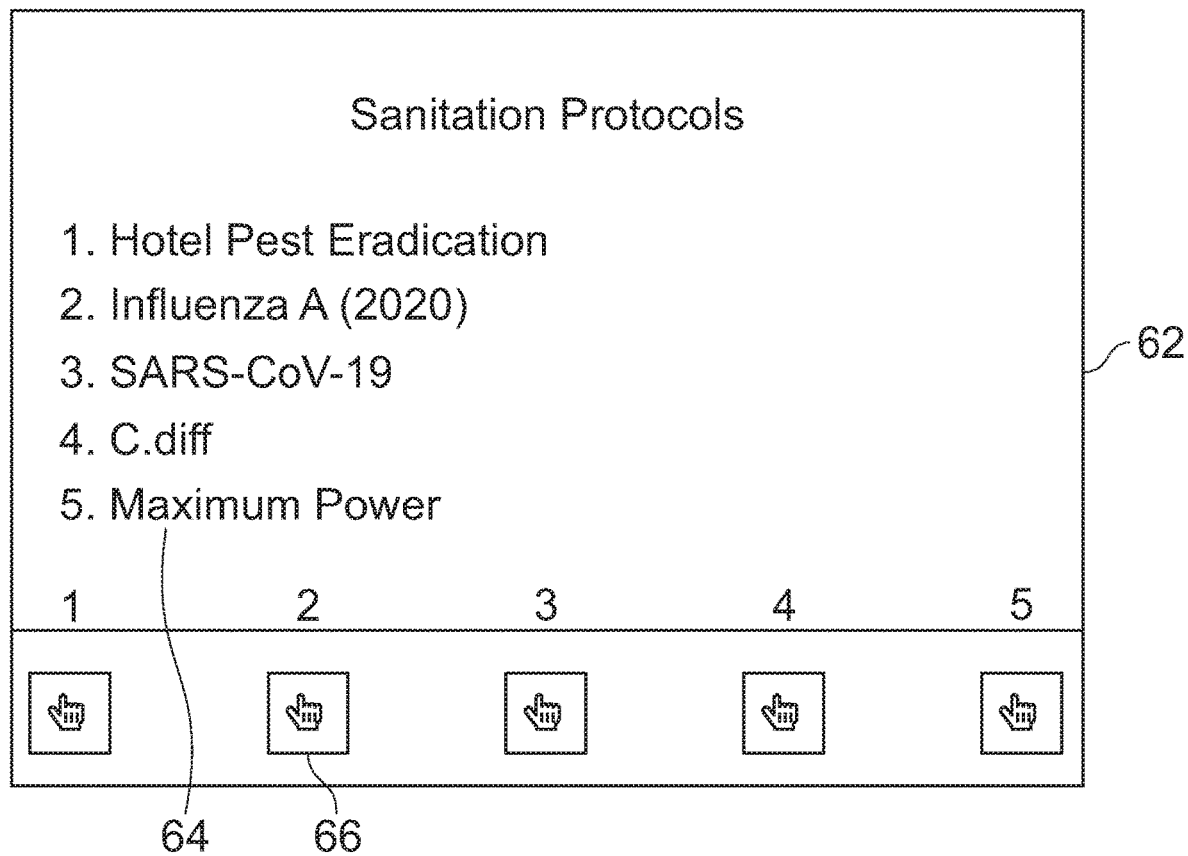
FIG. 6 is a diagram illustrating an example display of a control panel comprising a portion of a software architecture and system for delivering selected sanitation protocols for multiple pathogens and pests in accordance with an example embodiment.
Figure 9:
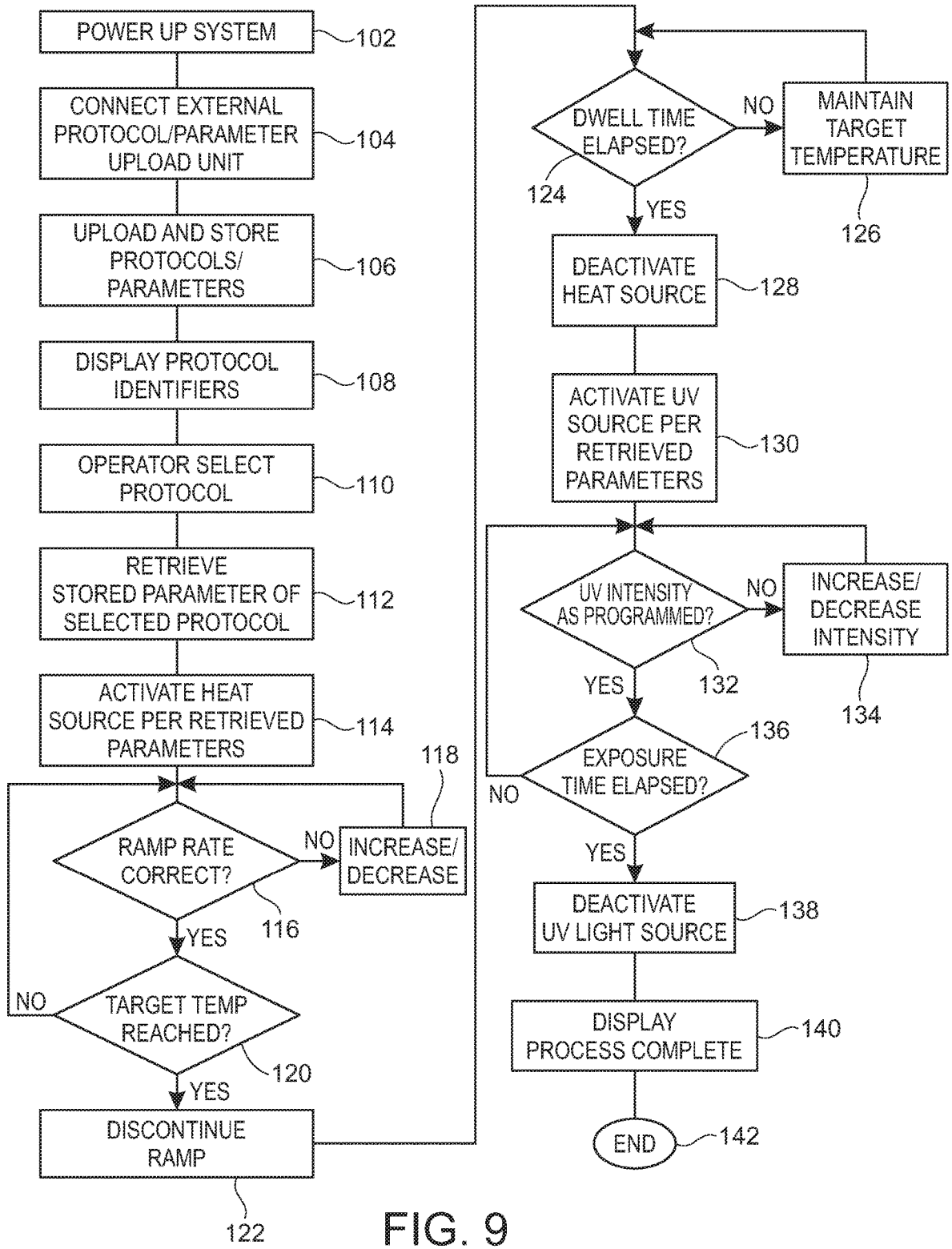
FIG. 9 is a flow chart illustrating an operation of a software architecture and system for delivering selected sanitation protocols for multiple pathogens and pests in accordance with an example embodiment.

As illustrated in FIG. 6, the control panel and display 62 is configured and adapted to receive from the controller 60 and to display on the display screen one or more sanitation protocol identifiers 64. Each displayed sanitation protocol identifier 64 corresponds and is linked to a sanitation protocol 65 stored in the sanitation protocol storage 68 as described above. While the sanitation protocol identifiers 64 are illustrated as a list of textual alphanumeric descriptions, it will be appreciated that is merely one example. The sanitation protocol identifiers 64 may comprise other forms such as icons or other graphical representations, and may be displayed in other arrangements such as a matrix or grid.

One or more of the sanitation protocol identifiers 64 may correspond to and be linked to stored sanitation protocols 65 for automatically treating specific target pathogens or target groups of pathogens, such as "SARS-CoV-19." One or more other sanitation protocol identifiers 64 may correspond to and be linked to stored sanitation protocols 65 for automatically eradicating certain pests or pests in a particular application, e.g., "Hotel Pest Eradication." Still other protocol identifiers 64 may correspond to and be linked to stored protocols to automatically control aspects of the operation of the software architecture and system 10, e.g., "Maximum Power." Preferably, the one or more protocol identifiers 64 comprise information from which the target pathogens, target groups of pathogens, target pests, target group of pests, or other control aspects may be readily identified. With regard to target pathogens and pests, for example, protocol identifiers 64 may include a common or recognized name of the target pathogens or pests. It will also be appreciated that one or more of the sanitation protocol identifiers 64 may correspond and be linked to stored protocols 65 that comprise a combination of these and other functions or operations of the software architecture and system 10.

The control panel and display 62 may also be adapted and configured to receive and display other information from the controller 60. Such data and information may include for example any of the operational or status information, telemetry and sensor data, logged data, etc. identified herein.

The control panel and display 62 also preferably comprises one or more inputs that are adapted for an operator or user to make selections of displayed choices and/or to input data and/or commands. The control panel and display 62 is adapted to communicate the selections, data, and/or commands to the controller 60. The inputs may comprise any suitable means of indicating a selection and/or inputting information. The inputs may comprise for example touch sensitive areas of the display screen, physical keys such as keys of a keyboard or keypad, and/or a wired or wireless pointing device such as a mouse or trackball.

The one or more inputs preferably comprise one or more protocol selectors 66 that are adapted for an operator or user to indicate a selection of a displayed sanitation protocol identifier 64 and thus a corresponding linked and stored sanitation protocol 65 and to communicate the selection to the controller 60. The protocol selectors 66 are illustrated for example purposes as a plurality of icons or keys with each icon or key corresponding to a displayed protocol identifier 64 by a corresponding number. It will be appreciated however that the one or more protocol selectors 66 may have other forms, for example a keypad adapted for a user to enter alphanumeric information corresponding to and/or identifying a selection of a displayed protocol identifier 64, or a pointing device with a switch adapted for a user to place a pointer on a selected protocol identifier 64 and indicate its selection with the switch.

The inputs may also comprise inputs in addition to the one or more protocol selectors 66. For example, one or more inputs may be provided for indicating a selection of information or data to be displayed on the display screen. One such input may indicate a selection to display a page comprising the sanitation protocol identifiers 64. Another input may indicate a selection to display a page comprising one or more different items of the operational or status information, telemetry and sensor data, logged data, etc. identified herein.

M. Portable Enclosure.

Some or all of the components of the software architecture and system for delivering selected sanitation protocols for multiple pathogens and pests 10 may be arranged on and/or in a portable enclosure 90. These may include one or more components of the fuel cell system 20 including the cooler 22, fuel storage 24, reformer 26, hydrogen purifier 28, hydrogen storage 30, and fuel cell stacks 32. They may also include one or more components of the electrical power system 40 including the power conditioning and regulation 42, the DC power storage 44, and the DC-AC conversion 46 components. They may also include the heat source 50, the controller 60, control panel/display 62, and one or more components of the UV light source 70.

The portable enclosure 90 may comprise wheels 92 or similar means to facilitate movement and positioning of the portable enclosure 90 and the components of the software architecture and system 10. For example, the portable enclosure 90 may be moved and positioned in or near a physical space or area to be sanitized, and may be removed therefrom after the physical space has been sanitized.

The portable enclosure 90 also may comprise an electrical connection 48 adapted for electrically coupling components of the software architecture and system 10 to a local electrical supply or microgrid, for example via a conventional AC electrical socket. As but one example, electrical connection 48 could be used to electrically couple an external battery charger to the DC power storage 44 component of the electrical power system 40 to charge the DC power storage 44 instead of the fuel cell system 20.

The portable enclosure 90 also may comprise one or more AC and/or DC electrical connections 49 which preferably are accessible externally of the portable enclosure 90. The one or more AC and/or DC electrical connections 49 are electrically coupled to the electrical power system 40 via suitable electrical wiring and components and may comprise standard AC and/or DC electrical connector types. The AC electrical connectors may be electrically coupled to the DC-AC converter 46 and the DC electrical connectors may be electrically coupled to the DC power storage 44 and/or the power conditioning and regulation component 42. As but one example, one or more telemetry devices and/or sensors comprising the telemetry and sensors 80 may be electrically coupled to and receive electrical power from the AC and/or DC electrical connectors 49. As another example, other devices external to and not comprising part of the software architecture and system 10 may be electrically coupled to the AC and/or DC electrical connectors 49 to receive electrical power, for example lights for lighting a physical space or area being sanitized.

N. External Upload Unit.

The external protocol/parameter upload unit 67 of the software architecture and system for delivering selected sanitation protocols for multiple pathogens and pests 10 is adapted and configured to upload and update the sanitation protocols 65 and parameters and values thereof in the protocol storage 68. The external protocol/parameter upload unit 67 may be coupled to and adapted to communicate with the controller 60 and the protocol storage 68 for those purposes. The external protocol/parameter upload unit 67 may be coupled and adapted to communicate with the controller 60 and the protocol storage 68 via a suitable wired or wireless network or direct connection, including the telecommunications network 12. Numerous wired and wireless data transmission protocols are suitable for this purpose.

Like the controller 60, the external protocol/parameter upload unit 67 may be comprised of any type of computer, processor, electronic controller, or other electronic logic and/or software that is suitable and adapted for uploading and updating sanitation protocols 65 and parameters thereof in the protocol storage 68. As one example, the external protocol/parameter upload unit 67 may comprise part of the mobile device 16.

The external protocol/parameter upload unit 67 may be electrically coupled to the electrical power system 40 via the AC/DC electrical connections 49 or otherwise to receive operating power. The external protocol/parameter upload unit 67 also may be coupled to an external power source through the electrical connection 48 or otherwise to receive operating power. The external protocol/parameter upload unit 67 also may have its own power source, such as batteries for providing operating power.

The external protocol/parameter upload unit 67 may be adapted to receive and store data comprising and corresponding to sanitation protocols 65 and the parameters thereof to be uploaded to the protocol storage 68. The external protocol/parameter upload unit 67 may comprise a user interface for that purpose. The user interface may comprise a display and an operator data input device, such as one or more of a keyboard, mouse, or other pointing and selection device, similar to the control panel and display 62.

The user interface may comprise an input form or template on the display adapted for an operator to enter data identifying the sanitation protocol 65 and the parameters and values thereof. The input form may have any suitable form. One suitable form may comprise a tabular form similar to that illustrated in FIG. 8 but including fields for entering all possible protocol and operational parameters and values supported by the software architecture and system 10 and necessary to carry out the sanitation protocol 65.

Using the input form and a suitable data input device, an operator may enter data for or comprising a new or existing sanitation protocol 65. The data will preferably include a protocol identifier 64 and one or more desired parameters and values of the sanitation protocol 65. The parameters may include the protocol and operational parameters described herein above with respect to the various components of the software architecture and system 10 as well as other operational parameters and values, for example system or process start and end times, delay times between steps of a sanitation process, sequences in which parameters and commands are to be performed, sensor sensitivity and filter settings, etc. The user interface will preferably include a "save" selection and the external protocol/parameter upload unit 67 will preferably be configured to respond to the "save" selection by storing the data for and comprising the sanitation protocol 65 after all desired parameters have been entered.

The external protocol/parameter upload unit 67 may be configured to determine if the entered protocol identifier 64 matches an existing saved protocol identifier 64 and to respond accordingly. If the entered protocol identifier 64 does not match an existing saved protocol identifier 64, the external protocol/parameter upload unit 67 preferably displays a version of the input form comprising blank fields corresponding to all of the possible parameters for sanitation protocols 65 that are supported by the system. The operator may enter desired parameter values in the blank fields for the desired parameter comprising the new sanitation protocol 65.

If the entered protocol identifier 64 matches an existing saved protocol identifier 64, the external protocol/parameter upload unit 67 may be configured to retrieve the previously saved parameters for the corresponding existing sanitation protocol 65 and prepopulate the input form on the display. The operator may then add to and/or edit the parameters comprising the sanitation protocol as desired and save the updated sanitation protocol 65.

The external protocol/parameter upload unit 64 may be configured to include an error checking function adapted to check the parameters of the new or updated sanitation protocol either as they are entered or saved. The error checking function may be adapted to report to the operator or even disallow saving parameters that are not allowable by the software architecture and system 10 or that perhaps conflict. Parameters could be disallowable because the entered values exceed the operating specifications of one or more components for example. Parameters could conflict because they involve an overlap or conflict between respective timed operations specified for one or more components for example.

The external protocol/parameter upload unit 67 may be configured to store, and to upload and update the sanitation protocols 65 and parameters thereof in the protocol storage 68 as one or more data files. In each file the parameters comprising a sanitation protocol 65 are preferable arranged as a collection of fixed or variable records in a tabular format, which may be similar to the tabular format illustrated in FIG. 8 for example. Each data file may comprise one complete sanitation protocol 65 or a plurality of complete sanitation protocols 65 with each sanitation protocol 65 comprising a section of the file. Each file or file section may also comprise only a portion of a sanitation protocol 65, for example only those parameters and values of a sanitation protocol 65 that are to be updated. When a file is to contain a plurality of sanitation protocols 65 or portions thereof, each section may be delineated in any suitable manner. For example, each section may be preceded by a header comprising a sanitation protocol identifier 64.

The external protocol/parameter upload unit 67 and/or the controller 60 are preferably configured to process the file contents accordingly to add new sanitation protocols 65 and/or to update existing sanitation protocols 65 in the protocol storage 68. For example, external protocol/parameter upload unit 67 may be configured to display a list of protocol identifiers 64 for an operator to select a new sanitation protocol 65 to be uploaded or an existing sanitation protocol 65 to be updated. The external protocol/parameter upload unit 67 may be configured to allow the operator to manually select whether a selected sanitation protocol 65 is to be uploaded and added to the protocol storage 68 as a new sanitation protocol 65 or whether an existing sanitation protocol 65 in the protocol storage 68 is to be updated using uploaded edited parameters of the selected sanitation protocol 65.

Alternatively, the external protocol/parameter upload unit 67 may be configured to automatically determine whether the selected sanitation protocol 65 is to be added to the protocol storage 68 as a new sanitation protocol 65 or whether an existing sanitation protocol 65 is to be updated. For example, the external protocol/parameter upload unit 67 may be configured to determine whether a sanitation protocol 65 is new or existing at the time an operator enters the protocol identifier 64 in the input form by comparing the entered protocol identifier 64 to a saved list of existing protocol identifiers 64 and setting a flag accordingly.

The external protocol/parameter upload unit 67 and/or the controller 60 should be configured to update all of the addresses and links necessary to access a sanitation protocol 65 in the protocol storage 68 when the sanitation protocol 65 is newly added or updated. This may include updating as necessary the links or addresses comprising the protocol identifiers 64 displayed in the control panel and display 62, and the links and addresses described above for the other stored sanitation protocols 65 in the protocol storage 68.

The external protocol/parameter upload unit 67 is thus adapted to enable sanitation protocols 65 and the parameters thereof to be easily created, edited, uploaded and updated in the software architecture and system 10. Thus, as new pathogen or pest targets or new treatment protocols are identified, new sanitation protocols 65 may be easily and quickly created and placed in use. Similarly, existing sanitation protocols 65 may be easily and quickly updated as new parameter combinations and values are shown to be effective. In both cases, older existing protocols may be retained for legacy operations or for future updating to meet new threats as they arise. It will be appreciated that the control and display 62 and/or the mobile device 16 may be configured to carry out some or all of the functions of the external protocol/parameter upload unit 67 as described above either in addition to it or in its place.

O. Operation of Preferred Embodiment.

In an example use of the software architecture and system for delivering selected sanitation protocols for multiple pathogens and pests 10, an operator or user first powers up 102 components of the system including the external protocol/parameter upload unit 67 and protocol storage 68, the controller 60. The operator or user may then use the user interface of the external protocol/parameter upload unit 67 to enter one or more protocol identifiers 64 and create one or more corresponding sanitation protocols 65.

Each sanitation protocol 65 defines a sanitation process to be carried out in a physical space or area to treat against one or more target pathogens and/or pests. As described herein, the parameters comprising each sanitation protocol 65 will be used by the controller 60 to control the components of the system to automatically carry out a sanitation process according to the parameters. The components to be controlled may include one or more components of the fuel cell system 20, the electrical power system 40, the heat source 50, the UV light source 70, and/or the telemetry and sensors 80 among others. The operator or user will preferably enter for each sanitation protocol 65 all of the protocol and operational parameters needed by the controller 60 to automatically carry out the desired sanitation process as described herein.

Once the protocol identifiers 64 and corresponding sanitation protocols 65 are created and all parameter values entered, the operator or user may use the user interface to store them in the external protocol/parameter upload unit 67. The operator or user may then connect 104 the external protocol/parameter upload unit 67 to the protocol storage 68 and use the user interface to cause the external protocol/parameter upload unit 67 to upload and store 106 the sanitation protocols 65 in the protocol storage 68 either directly or in cooperation with the controller 60. Preferably the control panel and display 62 also receives access to the protocol identifiers 64 and the corresponding sanitation protocols 65 via the controller 60.

The operator or user may then position the software architecture and system 10 in or near a physical space or area to be sanitized. For example, if the software architecture and system 10 is contained in and/or supported on a portable enclosure 90, the operator or user may move the portable enclosure 90 into a desired position in or near the physical space or area. The operator or user may also position one or more UV light sources 70 and one or more telemetry devices and/or sensors of the telemetry and sensors 80 in desired locations within the physical space or area and make any necessary connections.

It is assumed that the DC power storage 44 of the electrical power system 40 is charged sufficiently to provide AC and/or DC operating power for the components of the system to be operated and controlled to carry out the sanitation process. The DC power storage 44 may have been previously charged preferably from electrical energy generated by the fuel cell system 20. The DC power storage 44 could also have been previously charged from an external power source for example via the microgrid electrical connection 48 of the electrical power system 40. To the extent operation of the system during the sanitation process requires the production of additional electrical energy to recharge the DC power storage 44, the parameters of the sanitation protocol 65 related to the operation of the hydrogen fuel cell system 20 provide for such additional production.

If the components of the system that are necessary to carry out a desired sanitation process are not already powered up and ready to operate, the operator or user may power them up. Once powered, the control panel and display 62 will display 108 a list of protocol identifiers 64. The operator or user may use the sanitation protocol selectors 66 to select 110 a desired protocol identifier 64.

The selected protocol identifier 64 is linked to a sanitation protocol 65 stored in the protocol storage 68. The control panel and display 62 communicates the selected protocol identifier 64 and link to the controller 60. The controller 60 processes the link, communicates with the protocol storage 68, and retrieves 112 the parameters and values of the corresponding sanitation protocol 65. The controller 60 then processes the parameters and values and uses them to control the components of the system in a closed-loop feedback and control arrangement to automatically carry out the sanitation process in the physical space or area according to the parameters of the selected sanitation protocol 65.

As one example of a sanitation process to be automatically carried out, the controller 60 may activate 114 the heat source 50 according to a retrieved parameter. The controller 60 may then determine if the ramp rate is correct 116 according to a retrieved ramp rate parameter. In order to do that, the controller 60 may be configured to control an internal or external clock or timer, take one or more readings from the heat source 50 and/or one or more temperature sensors in the physical space being sanitized, calculate the temperature ramp, and compare it to the retrieved ramp rate parameter. If the controller 60 determines the ramp rate is not correct, i.e., is not as specified by the retrieved parameter, it may take action to control the heat source 50 to increase or decrease the ramp rate 118 and then again check the temperature, calculate the ramp rate, and determine if it is correct.

If the controller 60 determines the ramp rate is correct, it may then determine if the target temperature has been reached 120 in the physical space. It may do this for example by taking readings from one or more temperature sensors in the physical space and comparing to a retrieved target temperature parameter. If the controller 60 determines the target temperature has not been reached, it continues checking the ramp rate and target temperature until it determines the ramp rate is correct and the target temperature has been reached.

Once the controller 60 determines that the target temperature has been reached, it may take action to discontinue the temperature ramp 122. For example, it may discontinue increasing the temperature setting of the heat source 50 and maintain the setting at a value to maintain the target temperature in the physical space.

Also once the controller 60 determines that the target temperature has been reached, it may begin determining if the dwell time has elapsed 124 according to a retrieved dwell time parameter. It may do this for example by controlling a timer, counter or clock to start and then periodically taking a reading and comparing it to the value of the retrieved dwell time parameter.

If the controller 60 determines that the dwell time has not elapsed, then it may continue to maintain the target temperature 126 in the physical space. It may do this for example by periodically taking temperature readings from one or more temperature sensors in the physical space and by controlling the heat setting of the heat source 50 accordingly as described above to maintain the target temperature.

If the controller 60 determines the dwell time has elapsed, it may deactivate 128 the heat source 50 and activate 130 the UV light source 70 according to a retrieved parameter. It will be appreciated that the controller 60 may control the heat source 50 and UV light source 70 so that they are activated and operated successively, for overlapping periods of time, or co-extensively in time depending on one or more sequence parameters of the selected sanitation protocol 65.

Once the UV light source 70 is activated, the controller 60 may determine 132 if the intensity of the UV light in the physical space is as specified by a retrieved UV intensity parameter. It may do this for example by taking readings from one or more UV light intensity sensors in the physical space and comparing one or more readings with the value of the retrieved UV intensity parameter.

If the controller 60 determines the UV intensity in the physical space is not as specified by the retrieved UV intensity parameter, it may control one or more UV light sources 70 to increase or decrease the UV intensity 134 as appropriate. It may then continue periodically checking the UV light intensity, determining if it is as specified by the retrieved UV intensity parameter, and controlling the UV light sources 70 to adjust the intensity to be as specified by the retrieved intensity parameter.

Also, once the controller 60 determines the UV light intensity is as specified by the retrieved UV intensity parameter, it may determine if the exposure time has elapsed 136 according to a retrieved exposure time parameter. It may do this for example by controlling a timer, counter or clock to start and then periodically taking a reading and comparing it to the value of the retrieved exposure time parameter. The controller 60 may start the timer, counter, or clock at the time it activates one or more UV light sources 70 or once it determines the UV light intensity is as specified in the retrieved UV intensity parameter, depending on one or more sequence parameters of the selected sanitation protocol 65.

If the controller 60 determines that the exposure time has not elapsed, then it may continue to check and maintain the UV light intensity in the physical space as described above and may continue to periodically take readings from the timer, counter, or clock and determine if the exposure time has elapsed.

Once the controller 60 determines the exposure time has elapsed, it may deactivate 138 the UV light source 70 according to a retrieved parameter. It may also display that the process is complete 140 on the control panel and display 62 and end 142 the sanitation process.

Once the sanitation process is ended, the operator or user may power down the components of the software architecture and system 10, make the necessary disconnections, and reposition the components of the software architecture and system 10 to another physical space or area to carry out another sanitation process as desired.

Any and all headings are for convenience only and have no limiting effect. Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. All publications, patent applications, patents, and other references mentioned herein are incorporated by reference in their entirety to the extent allowed by applicable law and regulations.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs), DVDs (digital video discs), and computer instruction signals embodied in a transmission medium (with or without a carrier wave upon which the signals are modulated). For example, the transmission medium may include a telecommunications network, such as the Internet.

At least one embodiment of a software architecture and system for delivering selected sanitation protocols for multiple pathogens and pests is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention. These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments may provide for a computer program product, comprising a computer usable medium having a computer-readable program code or program instructions embodied therein, the computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

The software architecture and system for delivering selected sanitation protocols for multiple pathogens and pests may be embodied in other specific forms without departing from the spirit or essential attributes thereof, and it is therefore desired that the present embodiment be considered in all respects as illustrative and not restrictive. Many modifications and other embodiments of the software architecture and system for delivering selected sanitation protocols for multiple pathogens and pests will come to mind to one skilled in the art to which this invention pertains and having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the software architecture and system for delivering selected sanitation protocols for multiple pathogens and pests, suitable methods and materials are described above. Thus, the software architecture and system for delivering selected sanitation protocols for multiple pathogens and pests is not intended to be limited to the embodiments shown, but is to be accorded the widest scope consistent with the principles and features disclosed herein.

What is claimed is:

1. A software architecture and system, comprising:
   a plurality of sanitation protocols for sanitizing a physical space against a plurality of pathogens or pests with each sanitation protocol being adapted to treat a corresponding target pathogen or pest or target group of pathogens or pests;
   a protocol storage for storing the plurality of sanitation protocols;
   a plurality of protocol identifiers with each protocol identifier being selectable and comprising a link to a corresponding sanitation protocol of the plurality of sanitation protocols;
   at least one of a heat source for heating the physical space, and a UV light source for irradiating the physical space with UV radiation;
   a fuel cell system that locally generates electrical operating power to power the at least one heat source for heating the physical space, wherein the fuel cell system includes a liquid fuel storage tank storing a liquid fuel that is supplied to a reformer that produces hydrogen gas and a hydrogen storage storing hydrogen gas that is produced by the reformer, wherein the hydrogen gas stored in the hydrogen storage is supplied to a fuel cell; and a controller coupled to the protocol storage and at least one of the heat source and the UV light source;

wherein the controller is configured to respond to a protocol identifier being selected to automatically control the at least one of the heat source and the UV light source according to the corresponding sanitation protocol to sanitize the physical space against the corresponding target pathogen or pest or target group of pathogens or pests.

2. The software architecture and system of claim 1, wherein the plurality of sanitation protocols is arranged in the protocol storage as a plurality of successive pages.

3. The software architecture and system of claim 1, wherein the plurality of sanitation protocols is arranged in the protocol storage as a plurality of pages linked in a chain.

4. The software architecture and system of claim 3, wherein the chain is a two-way chain.

5. The software architecture and system of claim 1, wherein each sanitation protocol of the plurality of sanitation protocols comprises a plurality of parameters for sanitizing the physical space.

6. The software architecture and system of claim 5, wherein the plurality of parameters comprise one or more of target temperature, temperature ramp rate, dwell time, UV light intensity, and exposure time.

7. The software architecture and system of claim 1, comprising a fuel cell system adapted to locally generate hydrogen and to locally generate electrical operating power from the hydrogen to power the heat source for heating the physical space.

8. The software architecture and system of claim 1, comprising at least one sensor in the physical space, and wherein the controller, at least one of the heat source and the UV light source, and the at least one sensor are coupled in a closed-loop feedback control arrangement.

9. The software architecture and system of claim 1, comprising a display for displaying at least some of the plurality of protocol identifiers and a protocol selector for selecting a displayed protocol identifier.

10. The software architecture and system of claim 9, wherein the controller is located at or near the physical space and the display and protocol selector are located remote from the controller.

11. The software architecture and system of claim 1, comprising an upload unit for uploading sanitation protocols to the protocol storage.

12. The software architecture and system of claim 11, wherein the upload unit is located remote from the protocol storage.

13. The software architecture and system of claim 11, wherein each sanitation protocol of the plurality of sanitation protocols comprises a plurality of parameters, and wherein the upload unit comprises a user interface for entering the protocol identifier and the plurality of parameters for each sanitation protocol.

14. The software architecture and system of claim 13, wherein the user interface comprises a displayed template comprising a plurality of fields for entering the protocol identifier and the plurality of parameters.

15. The software architecture and system of claim 1, wherein a portable enclosure supports the at least one of the heat source and the controller.

16. The software architecture and system of claim 1, wherein the liquid fuel comprises a combination of methanol and deionized water.

17. A software architecture and system, comprising:
a portable enclosure comprising a hydrogen fuel cell adapted to locally generate hydrogen and to locally generate electrical operating power from the hydrogen, wherein the portable enclosure is adapted to be moved into or near a physical space;

a heat source for heating the physical space, wherein the heat source is adapted to receive electrical operating power from the hydrogen fuel cell;

a UV light source for irradiating the physical space with UV radiation, wherein the UV light source is adapted to be positioned in the physical space and to receive electrical operating power from the hydrogen fuel cell;

a sensor for sensing a physical condition in the physical space, wherein the sensor is adapted to be positioned in the physical space and to provide sensor data indicative of the physical condition;

a protocol storage;

a plurality of sanitation protocols for sanitizing the physical space against a plurality of pathogens or pests with each sanitation protocol being adapted to treat a corresponding target pathogen or pest or target group of pathogens or pests;

wherein the plurality of sanitation protocols are stored in the protocol storage as a plurality of pages, and wherein each sanitation protocol comprises a plurality of parameters;

a plurality of protocol identifiers with each protocol identifier being selectable and comprising a link to a corresponding sanitation protocol of the plurality of sanitation protocols;

a display for displaying at least some of the plurality of protocol identifiers and a protocol selector for selecting a displayed protocol identifier; and a controller coupled to the heat source, the UV light source and the sensor, wherein the controller is configured to respond to a protocol identifier being selected to automatically control the operation of the heat source and the UV light source according to the plurality of parameters of the corresponding sanitation protocol to sanitize the physical space against the corresponding target pathogen or pest or target group of pathogens or pests, and wherein the controller, the heat source, the UV light source, and the sensor are operable in a closed-loop feedback control arrangement.

18. The software architecture and system of claim 17, wherein the controller, the display, and the protocol selector are supported in or on the portable enclosure, and are adapted to receive electrical operating power from the hydrogen fuel cell.

19. The software architecture and system of claim 17, wherein the plurality of pages are linked in a chain.

20. The software architecture and system of claim 17, wherein the plurality of parameters comprise one or more of target temperature, temperature ramp rate, dwell time, UV light intensity, and exposure time.

21. The software architecture and system of claim 17, comprising an upload unit for receiving and uploading sanitation protocols to the protocol storage, wherein the upload unit is located remote from the protocol storage, wherein the upload unit comprises a user interface for entering the protocol identifier and the plurality of parameters for each sanitation protocol, and wherein the user interface comprises a displayed template comprising a plurality of fields for entering the protocol identifier and the plurality of parameters.

* * * * *